(12) United States Patent
Indukuri et al.

(10) Patent No.: US 9,650,346 B2
(45) Date of Patent: May 16, 2017

(54) SOLID FORMS OF ANTIRETROVIRAL COMPOUNDS, PROCESS FOR THE PREPARATION AND THEIR PHARMACEUTICAL COMPOSITION THEREOF

(75) Inventors: Venkata S. Indukuri, Hyderabad (IN); Vamsee K. Muppidi, Hyderabad (IN); Sree R. Joga, Hyderabad (IN); Seeta R. Gorantla, Hyderabad (IN); Satyanarayana Chava, Hyderabad (IN)

(73) Assignee: Laurus Labs Private Ltd. (IN)

( * ) Notice: Subject to any disclaimer, the term of this patent is extended or adjusted under 35 U.S.C. 154(b) by 0 days.

(21) Appl. No.: 13/985,172

(22) PCT Filed: Apr. 9, 2012

(86) PCT No.: PCT/IN2012/000256
§ 371 (c)(1),
(2), (4) Date: Dec. 9, 2013

(87) PCT Pub. No.: WO2012/137227
PCT Pub. Date: Oct. 11, 2012

(65) Prior Publication Data
US 2014/0094475 A1    Apr. 3, 2014

(30) Foreign Application Priority Data

Apr. 8, 2011  (IN) .......................... 1230/CHE/2011
Nov. 11, 2011 (IN) .......................... 3876/CHE/2011

(51) Int. Cl.
| | | |
|---|---|---|
| A01N 57/00 | (2006.01) |
| A61K 31/675 | (2006.01) |
| C07D 235/06 | (2006.01) |
| A61K 31/513 | (2006.01) |
| A61K 31/519 | (2006.01) |
| C07D 417/04 | (2006.01) |
| C07D 473/16 | (2006.01) |
| C07F 9/6561 | (2006.01) |
| C07D 411/04 | (2006.01) |

(52) U.S. Cl.
CPC .......... *C07D 235/06* (2013.01); *A61K 31/513* (2013.01); *A61K 31/519* (2013.01); *A61K 31/675* (2013.01); *C07D 411/04* (2013.01); *C07D 417/04* (2013.01); *C07D 473/16* (2013.01); *C07F 9/65616* (2013.01)

(58) Field of Classification Search
USPC ........................................................ 514/89
See application file for complete search history.

(56) References Cited

U.S. PATENT DOCUMENTS

| | | | |
|---|---|---|---|
| 2007/0197480 A1 * | 8/2007 | Scheller et al. | ............... 514/114 |
| 2008/0194539 A1 * | 8/2008 | Gmeiner et al. | ......... 514/211.09 |
| 2010/0216822 A1 | 8/2010 | Yuan | |
| 2010/0311761 A1 * | 12/2010 | Wunsch et al. | ............... 514/249 |

FOREIGN PATENT DOCUMENTS

| | | | |
|---|---|---|---|
| CN | 010712692 | * | 5/2010 |
| CN | 101712692 | * | 5/2010 |
| CN | 101712692 A | | 5/2010 |
| CN | 101987106 A | | 3/2011 |
| CN | 102232923 A | | 11/2011 |
| WO | 9403467 A2 | | 2/1994 |
| WO | WO-2006/133632 A1 | | 12/2006 |
| WO | WO 2009/074351 | * | 6/2009 |

OTHER PUBLICATIONS

Bastin et. al. (Organic process Research and Development (2000) 4:427-435).*

* cited by examiner

*Primary Examiner* — Marcos Sznaidman
(74) *Attorney, Agent, or Firm* — Blank Rome LLP

(57) ABSTRACT

Disclosed are solid forms of antiretroviral compounds and anti-oxidative acids, and processes for their preparation. Pharmaceutical compositions using the solid forms are also disclosed.

9 Claims, 21 Drawing Sheets

SOLID FORMS OF ANTIRETROVIRAL COMPOUNDS, PROCESS FOR THE PREPARATION AND THEIR PHARMACEUTICAL COMPOSITION THEREOF

CROSS-REFERENCE TO RELATED APPLICATIONS

The present application claims the benefit of International Patent Application No. PCT/IN2012/000256 filed Apr. 9, 2012, which in turn claims priority to Indian Patent Application No. 1230/CHE/2011, filed Apr. 8, 2011 and Indian Patent Application No. 3876/CHE/2011, filed Nov. 11, 2011, the entire disclosures which are incorporated herein by reference.

FIELD OF THE INVENTION

The present invention generally relates to solid forms of antiretroviral compounds, in particular combinations of antiretroviral compounds with anti-oxidative acids, processes for its preparation and a pharmaceutical composition containing the same.

BACKGROUND OF THE INVENTION

Antiretroviral (ARV) drugs are medications for the treatment of infection by retroviruses, primarily human immunodeficiency virus (HIV). The American national institutes of health and other organizations recommend offering antiretroviral treatment to all patients with acquired immune deficiency syndrome (AIDS).

Among the antiretroviral drugs which have been developed are those which target the HIV reverse transcriptase (RT) enzyme or protease enzyme, both of which enzymes are necessary for the replication of the virus. Examples of RT inhibitors include nucleoside/nucleotide RT inhibitors (NRTIs) and non-nucleoside RT inhibitors (NNRTIs). Currently, HIV-infected patients are routinely being treated with three-drug combinations. Regimens containing (at least) three NRTIs; two NRTIs in combination with one or two protease inhibitors (PI)(s); or two NRTIs in combination with a NNRTI, are widely used.

Clinical studies have shown that three-drug combinations of these anti-HIV drugs are much more effective than one drug used alone or two-drug combinations in preventing disease progression and death. Numerous studies of drug combinations with various combinations of such drugs have established that such combinations greatly reduce disease progression and deaths in people with HIV infections. The name now commonly given to combinations of anti-HIV drugs is HAART (Highly Active Anti-Retroviral Therapy).

A variety of antiretroviral drugs approved by the United States Food and Drug Administration (USFDA) and were commercially available in various dosage forms and strengths; for example Lamivudine, Stavudine, Zidovudine, Ritonavir, Saquinavir, Abacavir, Entecavir, Darunavir, Nevirapine, Efavirenz, Tenofovir disoproxil, Emtricitabine, Atazanavir and Raltegravir etc.

Antiretroviral drugs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different solvates or hydrate states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapour pressure, density, color, and compressibility.

PCT publication WO 99/05150 discloses tenofovir disoproxil fumarate characterized by powder X-ray diffraction (PXRD) and differential scanning calorimeter (DSC).

PCT publication WO 2009/074351 discloses solid forms of tenofovir disoproxil acid addition salts selected from the group consisting of succinic acid, tartaric acid, saccharic acid, citric acid, oxalic acid and salicylic acid. The '351 publication discloses characterization of the solid forms by PXRD peaks.

CN Publication No. 101712692 discloses tenofovir disoproxil acid addition salts including hydrochloric acid, sulfuric acid, phosphoric acid, toluene sulfonic acid, salicylic acid, benzoic acid, formic acid, citric acid, fumaric acid, maleic acid, malic acid.

U.S. Pat. No. 6,329,522 discloses Lamivudine and its acid addition salt such as salicylic acid and process for the preparation of the same.

PCT publication WO 2010/082128 discloses Lamivudine succinic acid and Lamivudine dicinnamic acid and process for the preparation of the same.

U.S. Pat. No. 6,294,540 discloses abacavir acid addition salts selected from sulfate, glutarate, benzoate, salicylate and dicarboxylate salts (glutarate, hemisuberate, adipate, fumarate, sebacate and pimelate). PCT publication WO 96/06844 discloses abacavir succinic acid salt.

U.S. Pat. No. 6,600,044 discloses emtricitabine acid addition salts such as methane sulfonic acid and hydrochloric acid.

It would be advantageous to have new forms of antiretroviral drugs that have improved properties, in particular, as oral formulations. Specifically, it is desirable to identify improved forms of the drug that exhibit significantly increased aqueous solubilities and stability. It is also desirable to increase the dissolution rate of drug-containing pharmaceutical compositions in water, increase the bioavailability of orally-administered compositions, and provide a more rapid onset to therapeutic effect. It is also desirable to have a form of the drug which, when administered to a subject, reaches a peak plasma level faster and/or has a longer lasting plasma concentration and higher overall exposure at high doses when compared to equivalent amounts of the drug in its presently-known form.

SUMMARY OF THE INVENTION

It has now been found that new solid forms of antiretroviral compounds; in particular combinations of antiretroviral compounds with anti-oxidative acids can be obtained which have improved properties as compared to presently-known form of such compounds. In an aspect, the improved property is selected from the group consisting of: increased solubility, increased dissolution, increased bioavailability, increased dose response, decreased hygroscopicity, decreased from diversity, more desired morphology, or other property described herein.

Accordingly, in one embodiment, the present invention provides solid forms of antiretroviral compounds and anti-oxidative acids (herein after referred to as "solid forms of antiretroviral compounds").

In accordance with a second embodiment, the present invention provides solid forms of antiretroviral compounds in combination with anti-oxidative acids; wherein the antiretroviral compounds includes, but are not limited to Nucleoside/Nucleotide Reverse Transcriptase Inhibitors (NRTIs), non Nucleoside Reverse Transcriptase Inhibitors (NNRTIs), Protease Inhibitors (PIs), Integrase Inhibitor, CCR5 Antagonist, and Fusion Inhibitor (FIs).

In accordance with a third embodiment, the present invention provides solid forms of antiretroviral compounds in combination with anti-oxidative acids; wherein the antiretroviral compounds includes, but are not limited to Lamivudine, Stavudine, Zidovudine, Didanosine, Delavirdine, Etravirine, Tipranavir, Indinavir, Saquinavir, Darunavir, Lopinavir, Fosamprenavir, Ritonavir, Nelfinavir, Enfuvirtide, Maraviroc, Abacavir, Atazanavir, Raltegravir, Entecavir, Tenofovir disoproxil, Rilpivirine, Nevirapine, Efavirenz, Emtricitabine, Acyclovir, Valacyclovir, Ganciclovir, Valganciclovir, Famciclovir, Oseltamivir and the like; wherein the anti-oxidative acids includes, but are not limited to benzoic acid derivatives such as p-hydroxy benzoic acid, Vanillic acid, Syringic acid, 3,4-dihydroxy benzoic acid and the like; cinnamic acid derivatives such as p-coumaric acid, Ferulic acid, Sinapic acid, Caffeic acid and the like.

In accordance with a fourth embodiment, the present invention further provides the solid forms of antiretroviral compounds exist in the form of salts, polymorphs of salts, co-crystals, or polymorphs of co-crystals.

In accordance with a fifth embodiment, the present invention provides a process for preparing solid forms of antiretroviral compounds comprising mixing; in solution an antiretroviral compound with an anti-oxidative acid compound under crystallization conditions sufficient to produce solid forms of antiretroviral compounds.

In accordance with a sixth embodiment, the present invention provides a process for preparing solid forms of antiretroviral compounds comprising; slurring in solution an antiretroviral compound with an anti-oxidative acid compound sufficient to produce solid forms of antiretroviral compounds.

In accordance with a seventh embodiment, the present invention provides a process for preparing solid forms of antiretroviral compounds comprising; grinding, heating, co-subliming, or co-melting an antiretroviral compound with an anti-oxidative acid compound under crystallization conditions, so as to form a solid forms of antiretroviral compounds.

In accordance with an eighth embodiment, the present invention provides a pharmaceutical composition comprising one or more of a therapeutically effective amount of solid forms of antiretroviral compounds prepared by the processes of the present invention.

In accordance with a ninth embodiment, the present invention provides a method of treating HIV infections comprising pharmaceutical composition containing one or more of therapeutically effective amount of solid forms of antiretroviral compounds of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
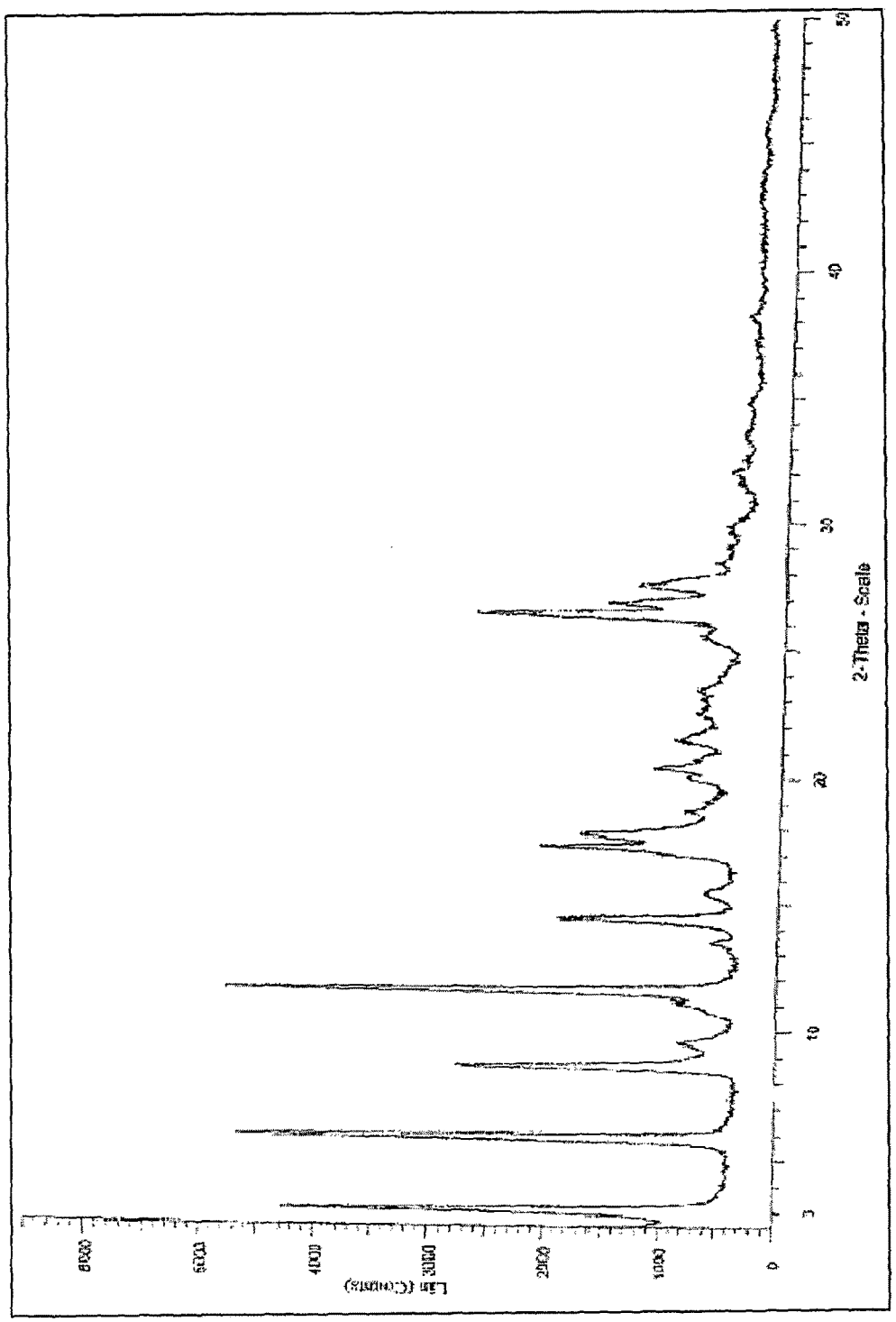
FIG. 1 is the characteristic powder X-ray diffraction (XRD) pattern of Tenofovir disoproxil ferulate Form AL1.

The present invention addresses a need in the art by providing new solid forms of antiretroviral compounds; in particular combinations of antiretroviral compounds with anti-oxidative acids and processes for their preparation.

The present inventors have identified novel solid forms of antiretroviral compounds, particularly in combination with anti-oxidative acids. These solid forms may be in the form of salts, polymorphs of salts, co-crystals, or polymorphs of co-crystals.

It has surprisingly been found that when an antiretroviral compound and a selected anti-oxidative acid component are allowed to form solid forms, the resulting solid forms may give rise to improved properties of the antiretroviral compound, as compared to the antiretroviral compound in a free form (including free acids, free bases, and zwitterions, hydrates, solvates, etc.), or an acid or base salt thereof particularly with respect to: solubility, dissolution, bioavailability, stability, Cmax, Tmax, processability, longer lasting therapeutic plasma concentration, hygroscopicity, decrease in form diversity (including polymorphism and crystal habit), change in morphology or crystal habit, etc. For example, a solid form of an antiretroviral compound is particularly advantageous where the original antiretroviral compound is insoluble or sparingly soluble in water. Additionally, the solid form properties conferred upon the antiretroviral compounds are also useful because the bioavailability of the antiretroviral compound can be improved and the plasma concentration and/or serum concentration of the antiretroviral compound can be improved. This is particularly advantageous for orally-administrable formulations. Moreover, the dose response of the antiretroviral compound can be improved, for example by increasing the maximum attainable response and/or increasing the potency of the antiretroviral compound by increasing the biological activity per dosing equivalent.

The anti oxidative acids used in the present invention are not only intended for formation of pharmaceutically acceptable salt form of antiretroviral compounds, itself can advantageously be use for the therapeutical use, for example, anti oxidative acids can stabilize the body's metabolism by defending against damage caused by free radicals. The anti oxidative acid salts of antiretroviral compounds are more effective with respect to therapeutic activity of the antiretroviral compound as compared to the antiretroviral compound salt form with non anti oxidative acids described in the afore mentioned literature.

Accordingly, in one embodiment, the present invention provides solid forms of antiretroviral compounds in combination with anti-oxidative acids (herein after referred to as "solid forms of antiretroviral compounds")

The ratio of antiretroviral compound to anti-oxidative acid compound may be stoichiometric or non-stoichiometric according to the present invention. For example, 1:1, 1.5:1, 1:1.5, 2:1 and 1:2 ratios of antiretroviral compound:anti-oxidative acid compound are acceptable.

In another embodiment, the antiretroviral compound selected from at least one of antiretroviral compounds known in the art. For example, the antiretroviral compound include, but are not limited to Nucleoside/Nucleotide Reverse Transcriptase Inhibitors (NRTIs), non Nucleoside Reverse Transcriptase Inhibitors (NNRTIs), Protease Inhibitors (PIs), Integrase Inhibitor, CCR5 Antagonist, Fusion Inhibitor (FIs).

In another embodiment, the antiretroviral compounds selected from at least one of Lamivudine, Stavudine, Zidovudine, Didanosine, Delavirdine, Etravirine, Tipranavir, Indinavir, Saquinavir, Darunavir, Lopinavir, Fosamprenavir, Ritonavir, Nelfinavir, Enfuvirtide, Maraviroc, Abacavir, Atazanavir, Raltegravir, Entecavir, Tenofovir disoproxil, Rilpivirine, Nevirapine, Efavirenz, Emtricitabine, Acyclovir, Valacyclovir, Ganciclovir, Valganciclovir, Famciclovir, Oseltamivir and the like.

In another embodiment, the anti-oxidative acid compound selected from at least one of anti-oxidative acid compounds known in the art. For example, the anti-oxidative acid includes, but are not limited to benzoic acid derivatives such as p-hydroxy benzoic acid, Vanillic acid, Syringic acid, 3,4-dihydroxy benzoic acid and the like; cinnamic acid derivatives such as p-coumaric acid, Ferulic acid, Sinapic acid, Caffeic acid and the like.

In a further embodiment, the difference in pKa value of the anti-oxidative acid compound and the antiretroviral compound is less than 2. In other embodiments, the difference in pKa values of the anti-oxidative acid compound and the antiretroviral compound is less than 5, less than 8, and less than 10.

In another embodiment, the present invention provides a process for preparing solid forms of antiretroviral compounds comprising; mixing in solution an antiretroviral compound with an anti-oxidative acid compound under crystallization conditions sufficient to produce solid forms of antiretroviral compounds.

The step of forming the solution includes any form of antiretroviral compound may dissolve in to a suitable solvent at a suitable temperature then anti-oxidant acid may be added to the solution. Alternatively, the solution may be formed by adding both antiretroviral compound and anti-oxidative acid at a time in to a suitable solvent. Preferably, first forming a solution of antiretroviral compound and then anti-oxidative acid added in to the solution of antiretroviral compound and solvent.

Suitable solvents include, but are not limited to water, lower alcohols, ketones, esters, ethers, $C_{5-7}$ linear, branched or cyclic, saturated or unsaturated hydrocarbons, nitriles, halogenated hydrocarbons, or mixtures thereof.

The lower alcohols include, but are not limited to $C_{1-4}$ alcohol such as methanol, ethanol, isopropanol, n-propanol, n-butanol, isobutanol and the like and mixtures thereof; ketones include, but are not limited to acetone, methyl ethyl ketone, methyl isobutyl ketone and like and mixtures thereof; esters include, but are not limited to methyl acetate, ethyl acetate, isopropyl acetate and the like and mixtures thereof; ethers include, but are not limited to tetrahydrofuran, dimethyl ether, diisopropyl ether, methyl tertiary butyl ether, 1,4-dioxane and the like and mixtures thereof; $C_{5-7}$ linear, branched or cyclic, saturated or unsaturated hydrocarbons include, but are not limited to toluene, xylene, n-pentane, n-hexane, n-heptane, cyclohexane, methyl cyclohexane and the like and mixtures thereof; nitriles include, but are not limited to acetonitrile, propionitrile and the like and mixtures thereof; halogenated hydrocarbons include, but are not limited to methylene chloride, ethylene chloride, chloroform, carbon tetrachloride and the like and mixtures thereof. Preferably the suitable solvents selected from the group consisting of methanol, ethanol, isopropanol, acetone, tetrahydrofuran, isopropyl ether, acetonitrile, hexane, cyclohexane, ethyl acetate, water and mixtures thereof.

Any conditions which forming the solid forms of antiretroviral compounds from solution may be used whereby solid forms of antiretroviral compounds formed. Conveniently, this step includes evaporation of the solvent so as to concentrate the solute whereby solid forms of antiretroviral compounds may be precipitated. In a preferred embodiment, the solution is first heated to ensure mixing and solid formation, followed by cooling so as to enable solid forms to precipitate.

The heating step may be carried out at a temperature of about ambient temperature to about reflux temperature of the solvent chosen. Typically, the solution is heated at a temperature of at least about 30° C. to about reflux. Preferably, the solution is heated at about 30° C. to about 80° C.

The precipitation of solid forms of antiretroviral compounds may be carried out by any process known in the art, for example crystallization, solvent precipitation, concentrated by subjecting the solution to heating, spray drying, freeze drying, evaporation on rotary evaporator under vacuum, agitated thin film evaporator (ATFE) and the like.

Optionally, a second solvent may be added to the solution of antiretroviral compounds and anti oxidative acid compounds before cooling to precipitation. The second solvent includes, but is not limited to water, ethers such as isopropyl ether; cyclic hydrocarbons such as n-pentane, n-hexane, n-heptane, cyclohexane and the like and mixtures thereof.

In another embodiment, the present invention provides a process for preparing solid forms of antiretroviral compounds comprising; slurring in solution an antiretroviral compound with an anti-oxidative acid compound sufficient to produce solid forms of antiretroviral compounds.

The solvent for the slurry may include any suitable solvent as described just above such as water, lower alcohols, ketones, esters, ethers, $C_{5-7}$ linear, branched or cyclic, saturated or unsaturated hydrocarbons, nitriles, halogenated hydrocarbons, or mixtures thereof.

Optionally, the slurry may be carried out at a temperature of about ambient temperature to about reflux temperature of the solvent chosen. Typically, the slurry is carried at a temperature of at least about 30° C. to about reflux, preferably at about 30° C. to about 80° C.

In an alternative embodiment, the antiretroviral compound mixed with the anti-oxidative acid compound in a solid phase. Any suitable means for mixing may be used in this step, including commercially-available solid mixers.

This may involve grinding or milling the two solids together or melting one or both components and allowing them to recrystallize. The use of a granulating liquid may improve or may impede solid formation. Non-limiting examples of tools useful for the formation of solid forms of antiretroviral compounds may include, for example, an extruder or a mortar and pestle. Further, contacting the antiretroviral compound with the anti-oxidative acid compound may also involve either solubilizing the antiretroviral compound and adding the anti-oxidative acid compound, or solubilizing the anti-oxidative acid compound and adding the antiretroviral compound. Crystallization conditions are applied to the antiretroviral compound and anti-oxidative acid compound. This may entail altering a property of the solution, such as pH or temperature and may require concentration of the solute, usually by removal of the solvent, typically by drying the solution. Solvent removal results in the concentration of both antiretroviral compound and anti-oxidative acid compound increasing over time so as to facilitate crystallization. For example, evaporation, cooling, co-sublimation, or the addition of an antisolvent may be used to crystallize solid forms. In another embodiment, a slurry comprising an antiretroviral compound and an anti-oxidative acid compound is used to form solid forms. Once the solid phase comprising any crystals is formed, this may be tested as described herein.

Some of the antiretroviral compounds and anti-oxidative acid compounds of the present invention have one or more chiral centers and may exist in a variety of stereoisomeric configurations. As a consequence of these chiral centers, several antiretroviral compounds and anti-oxidative acid compounds of the present invention occur as racemates, mixtures of enantiomers and as individual enantiomers, as well as diastereomers and mixtures of diastereomers. All such racemates, enantiomers, and diastereomers are within the scope of the present invention including, for example, cis- and trans-isomers, R- and S-enantiomers, and (D)- and (L)-isomers.

The solid forms of antiretroviral compounds recovered using the process of the present invention described above may include one or more of antiretroviral compounds such as Tenofovir disoproxil, Lamivudine, Emtricitabine and Abacavir with combination of one or more of anti-oxidative acid compounds such as ferulic acid, caffeic acid, p-coumaric acid and sinapic acid.

Tenofovir disoproxil, Lamivudine, Emtricitabine and Abacavir can be represented by the structure as follows:

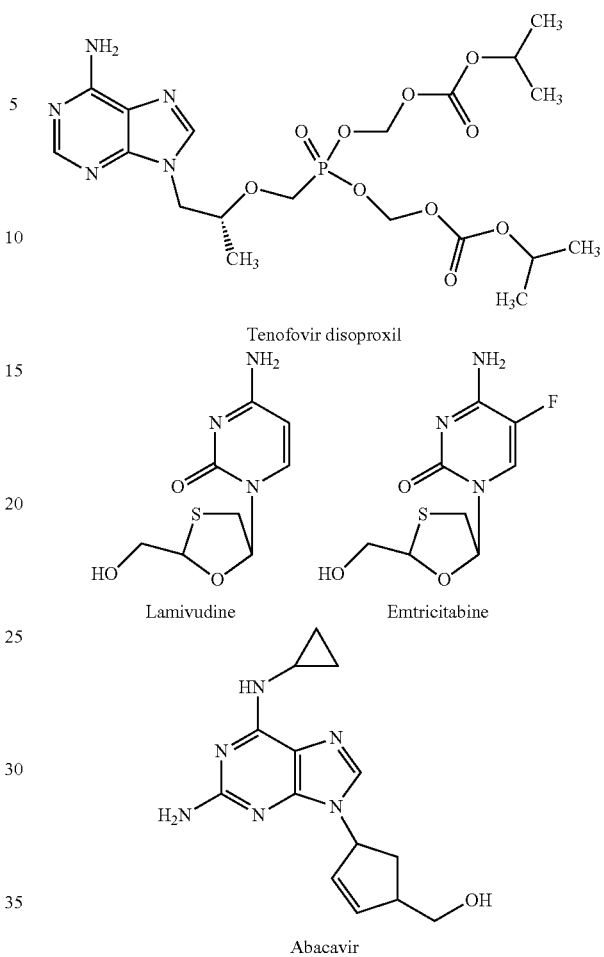

Tenofovir disoproxil

Lamivudine

Emtricitabine

Abacavir

In another embodiment, the present invention provides Tenofovir disoproxil ferulate.

In another embodiment, the present invention provides Tenofovir disoproxil ferulate in crystalline Form AL1.

In another embodiment, the present invention further provides Tenofovir disoproxil ferulate in crystalline Form AL1, characterized by an X-Ray diffraction (XRD) pattern substantially in accordance with FIG. 1.

In another embodiment, the present invention provides Tenofovir disoproxil ferulate in crystalline Form AL2.

Figure 2:
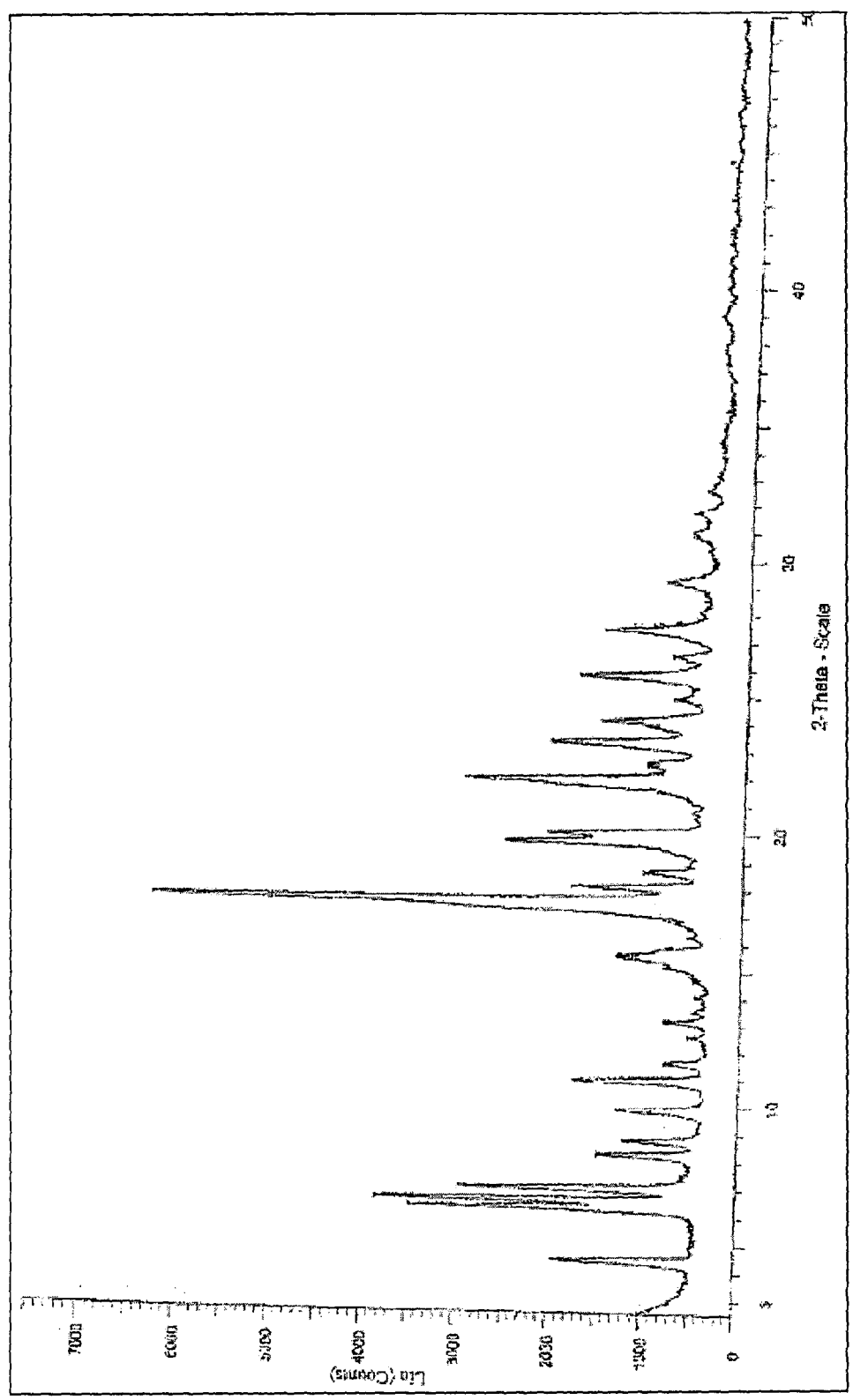
FIG. 2 is the characteristic powder X-ray diffraction (XRD) pattern of Tenofovir disoproxil ferulate Form AL2.

In another embodiment, the present invention further provides Tenofovir disoproxil ferulate in crystalline Form AL2, characterized by an X-Ray diffraction (XRD) pattern substantially in accordance with FIG. 2.

In another embodiment, the present invention provides Tenofovir disoproxil ferulate in crystalline Form AL3.

Figure 3:
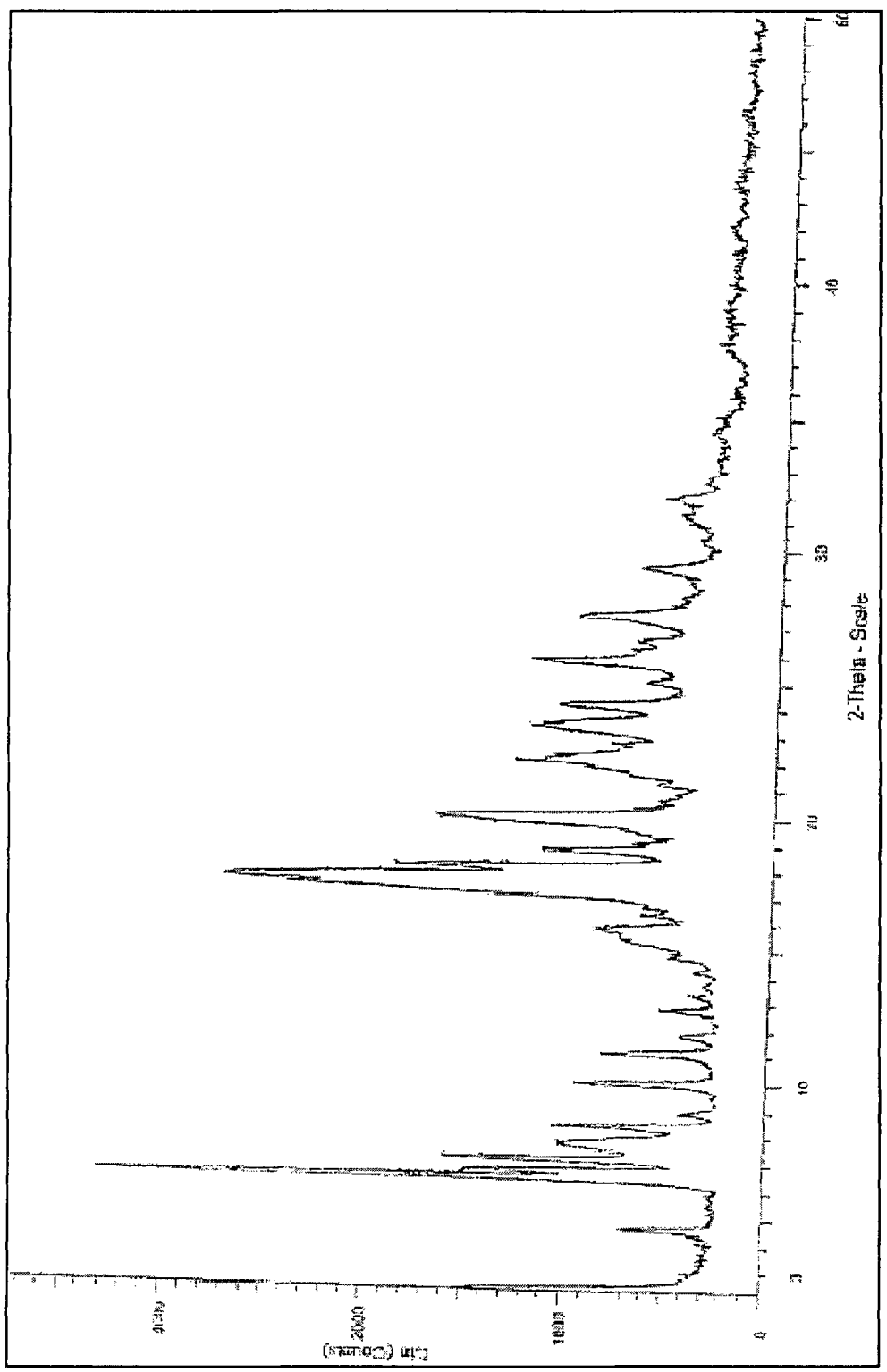
FIG. 3 is the characteristic powder X-ray diffraction (XRD) pattern of Tenofovir disoproxil ferulate Form AL3.

In another embodiment, the present invention further provides Tenofovir disoproxil ferulate in crystalline Form AL3, characterized by an X-Ray diffraction (XRD) pattern substantially in accordance with FIG. 3.

In another embodiment, the present invention provides Tenofovir disoproxil ferulate in crystalline Form AL4.

Figure 4:
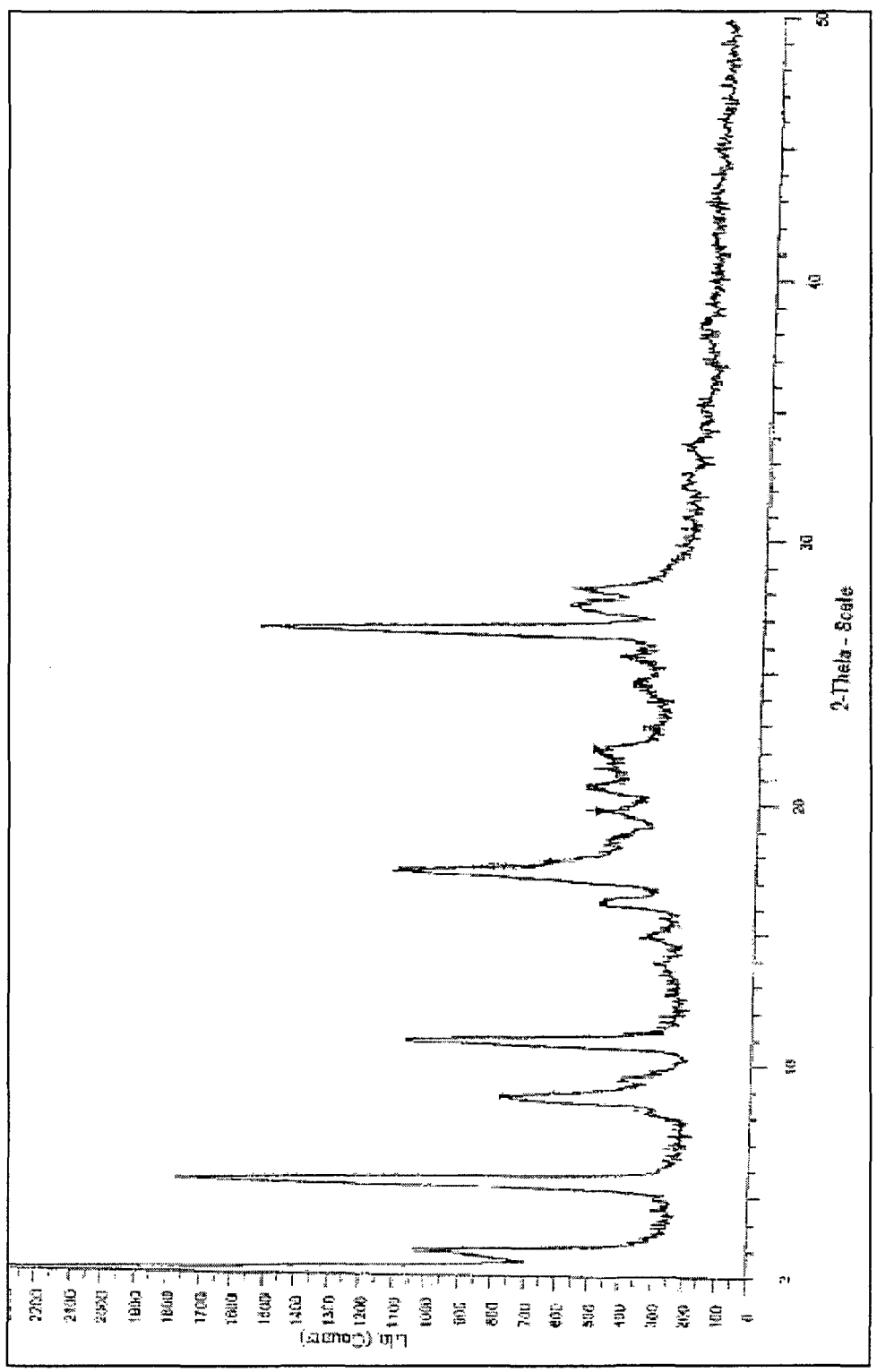
FIG. 4 is the characteristic powder X-ray diffraction (XRD) pattern of Tenofovir disoproxil ferulate Form AL4.

In another embodiment, the present invention further provides Tenofovir disoproxil ferulate in crystalline Form AL4, characterized by an X-Ray diffraction (XRD) pattern substantially in accordance with FIG. 4.

In another embodiment, the present invention provides Tenofovir disoproxil ferulate in crystalline Form AL5.

Figure 5:
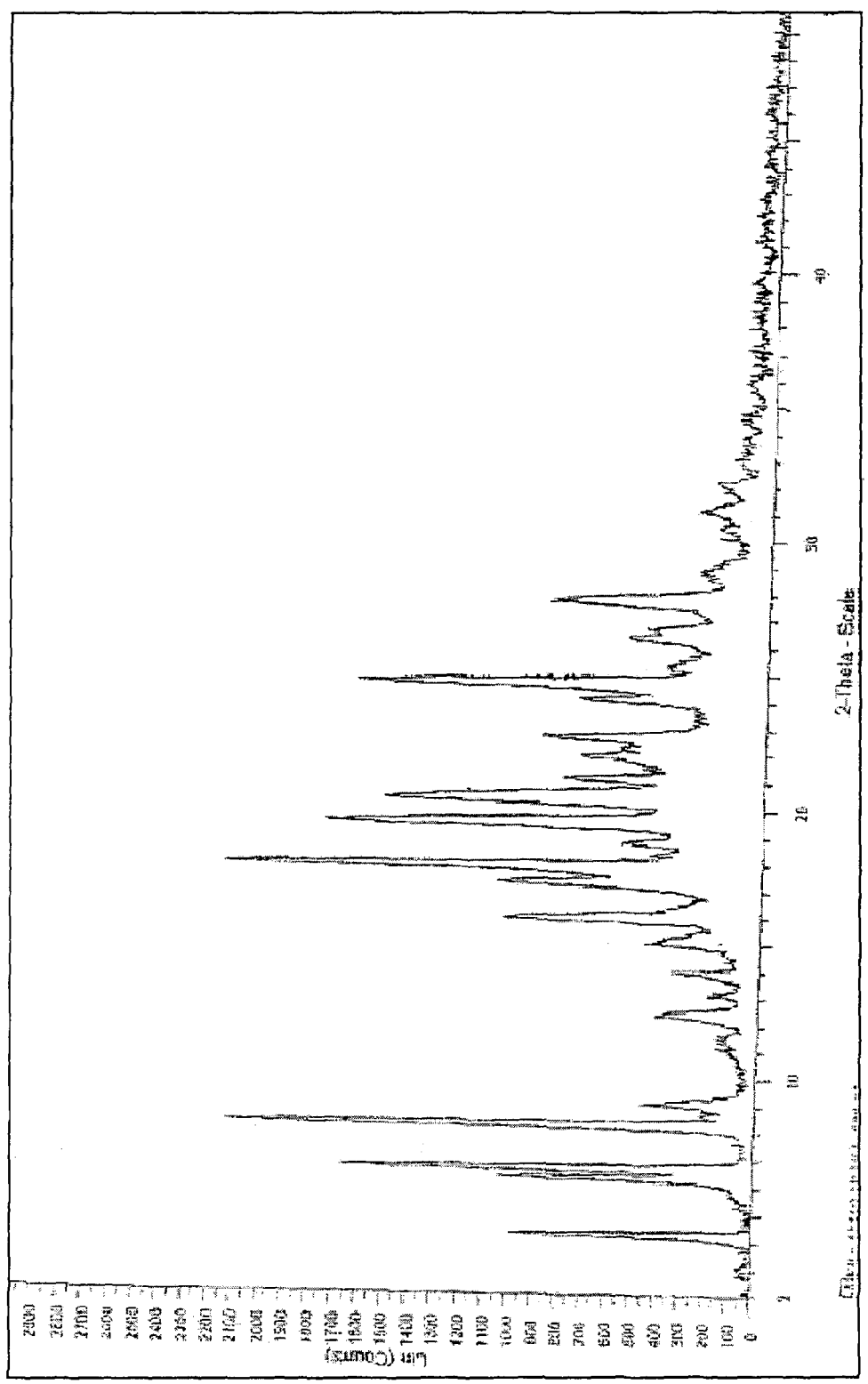
FIG. 5 is the characteristic powder X-ray diffraction (XRD) pattern of Tenofovir disoproxil ferulate Form AL5.

In another embodiment, the present invention further provides Tenofovir disoproxil ferulate in crystalline Form AL5, characterized by an X-Ray diffraction (XRD) pattern substantially in accordance with FIG. 5.

In another embodiment, the present invention provides Tenofovir disoproxil caffeate.

In another embodiment, the present invention provides Tenofovir disoproxil caffeate in crystalline Form I.

Figure 6:
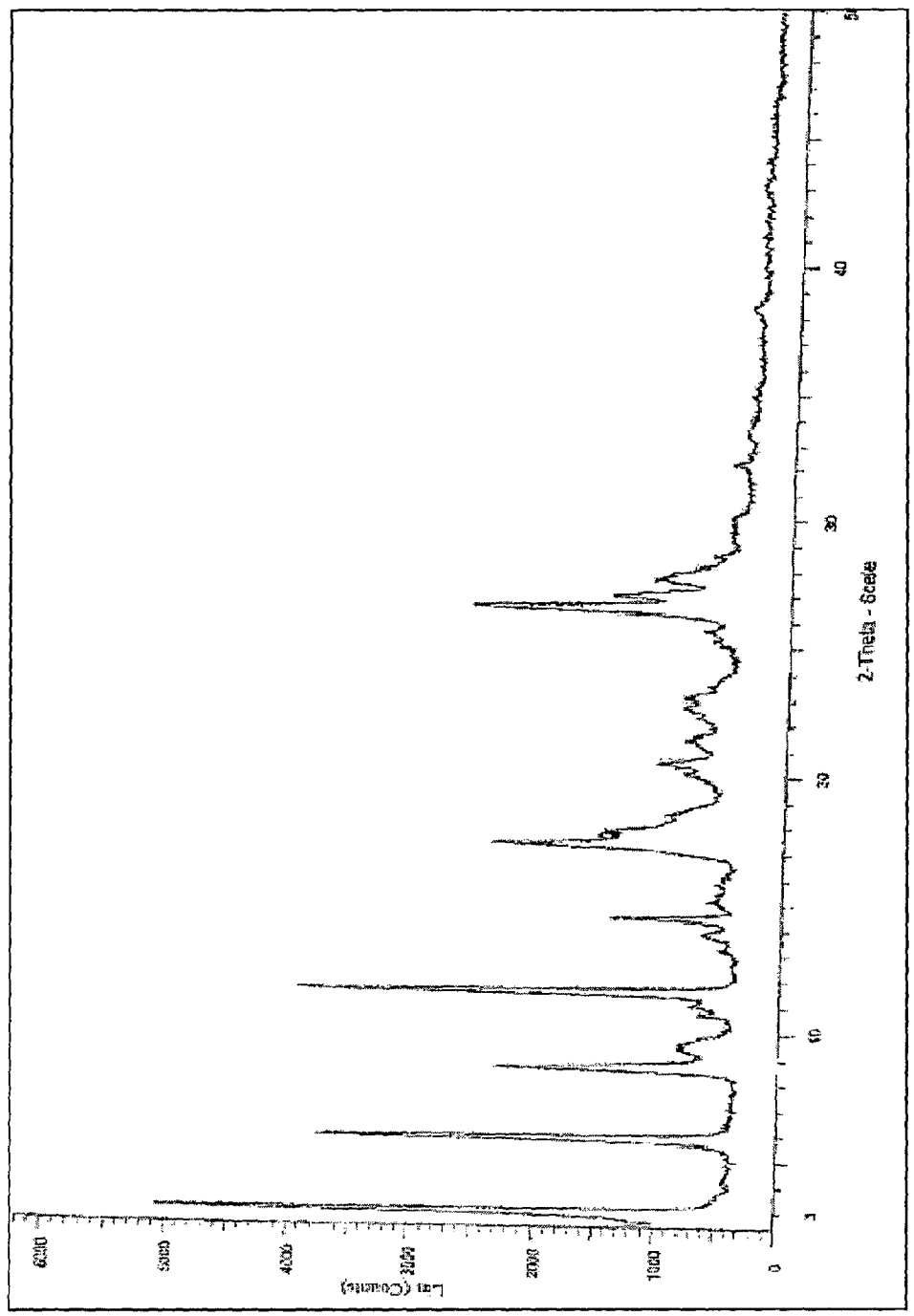
FIG. 6 is the characteristic powder X-ray diffraction (XRD) pattern of Tenofovir disoproxil caffeate Form I.

In another embodiment, the present invention further provides Tenofovir disoproxil caffeate in crystalline Form I characterized by an X-Ray diffraction (XRD) pattern substantially in accordance with FIG. 6.

In another embodiment, the present invention provides Tenofovir disoproxil caffeate in crystalline Form II.

Figure 7:
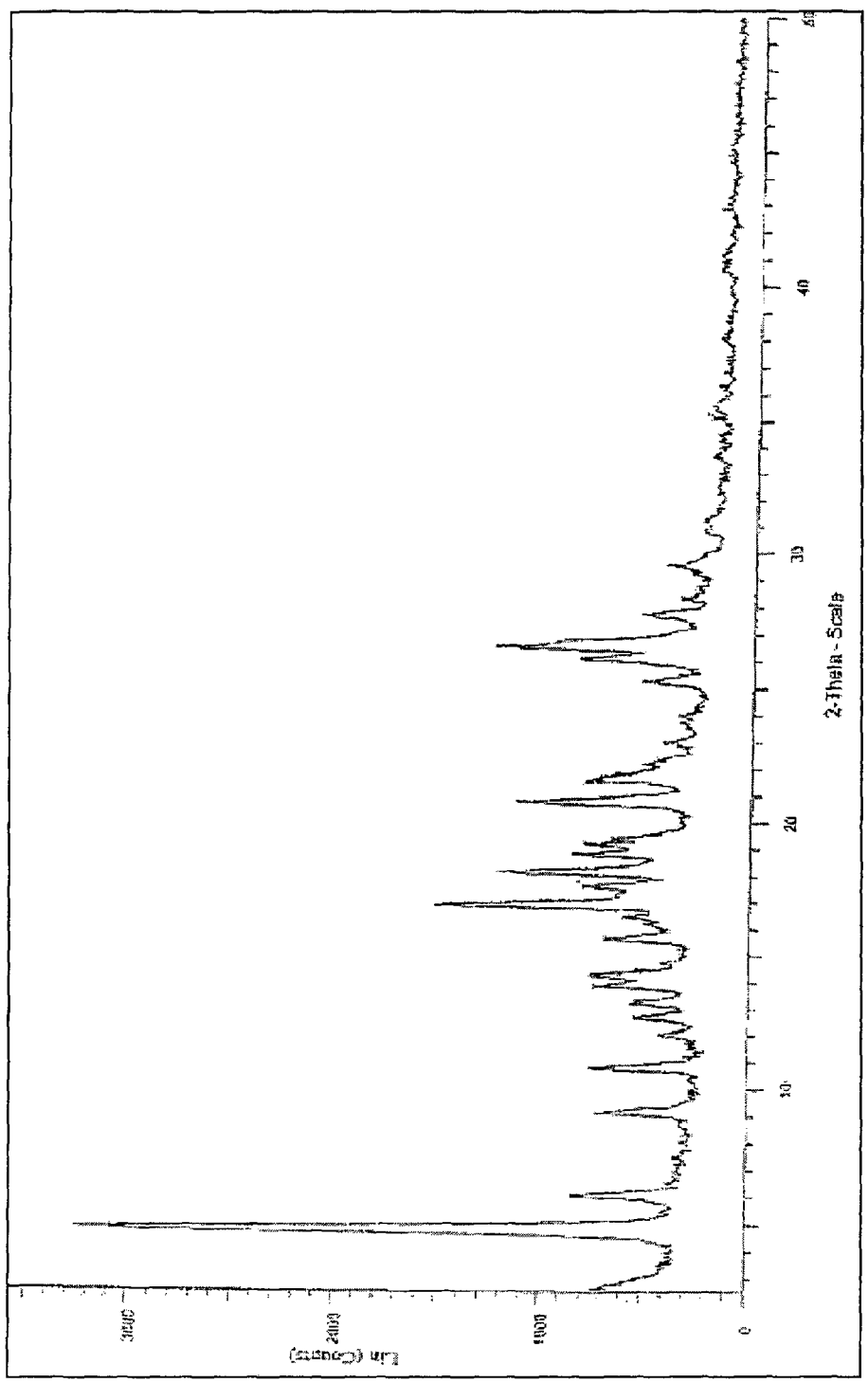
FIG. 7 is the characteristic powder. X-ray diffraction (XRD) pattern of Tenofovir disoproxil caffeate Form II.

In another embodiment, the present invention further provides Tenofovir disoproxil caffeate in crystalline Form II characterized by an X-Ray diffraction (XRD) pattern substantially in accordance with FIG. 7.

In another embodiment, the present invention provides Tenofovir disoproxil p-coumarate.

In another embodiment, the present invention provides Tenofovir disoproxil p-coumarate in crystalline Form I.

Figure 8:
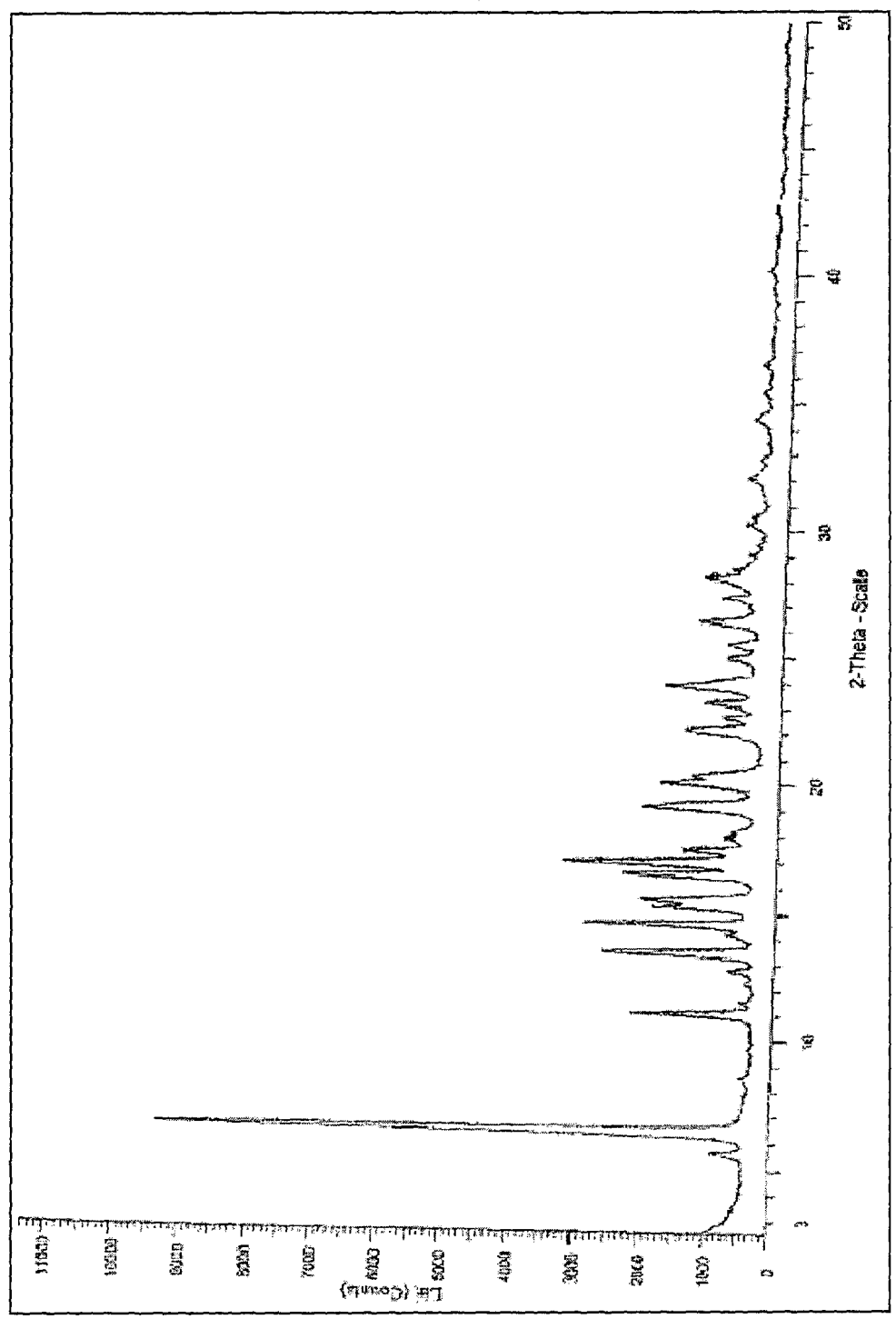
FIG. 8 is the characteristic powder X-ray diffraction (XRD) pattern of Tenofovir disoproxil p-coumarate Form I.

In another embodiment, the present invention further provides Tenofovir disoproxil p-coumarate in crystalline Form I, characterized by an X-Ray diffraction (XRD) pattern substantially in accordance with FIG. 8.

In another embodiment, the present invention provides Tenofovir disoproxil sinapate.

In another embodiment, the present invention provides Tenofovir disoproxil sinapate in crystalline Form I.

Figure 9:
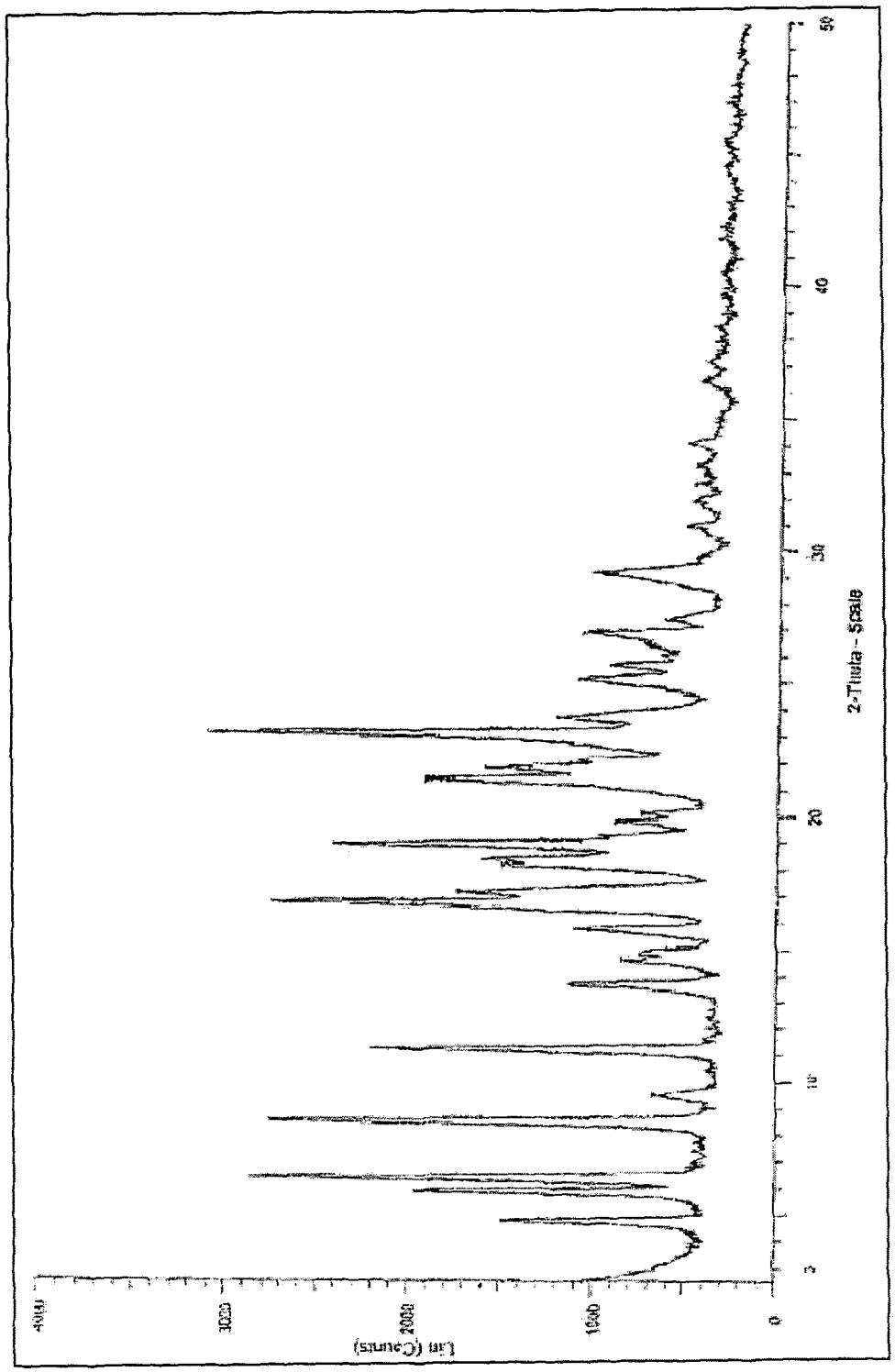
FIG. 9 is the characteristic powder X-ray diffraction (XRD) pattern of Tenofovir disoproxil sinapate Form I.

In another embodiment, the present invention further provides solid form of Tenofovir disoproxil sinapate in crystalline Form I, characterized by an X-Ray diffraction (XRD) pattern substantially in accordance with FIG. 9.

In another embodiment, the present invention provides Lamivudine caffeate.

In another embodiment, the present invention provides Lamivudine caffeate in crystalline Form I.

Figure 10:
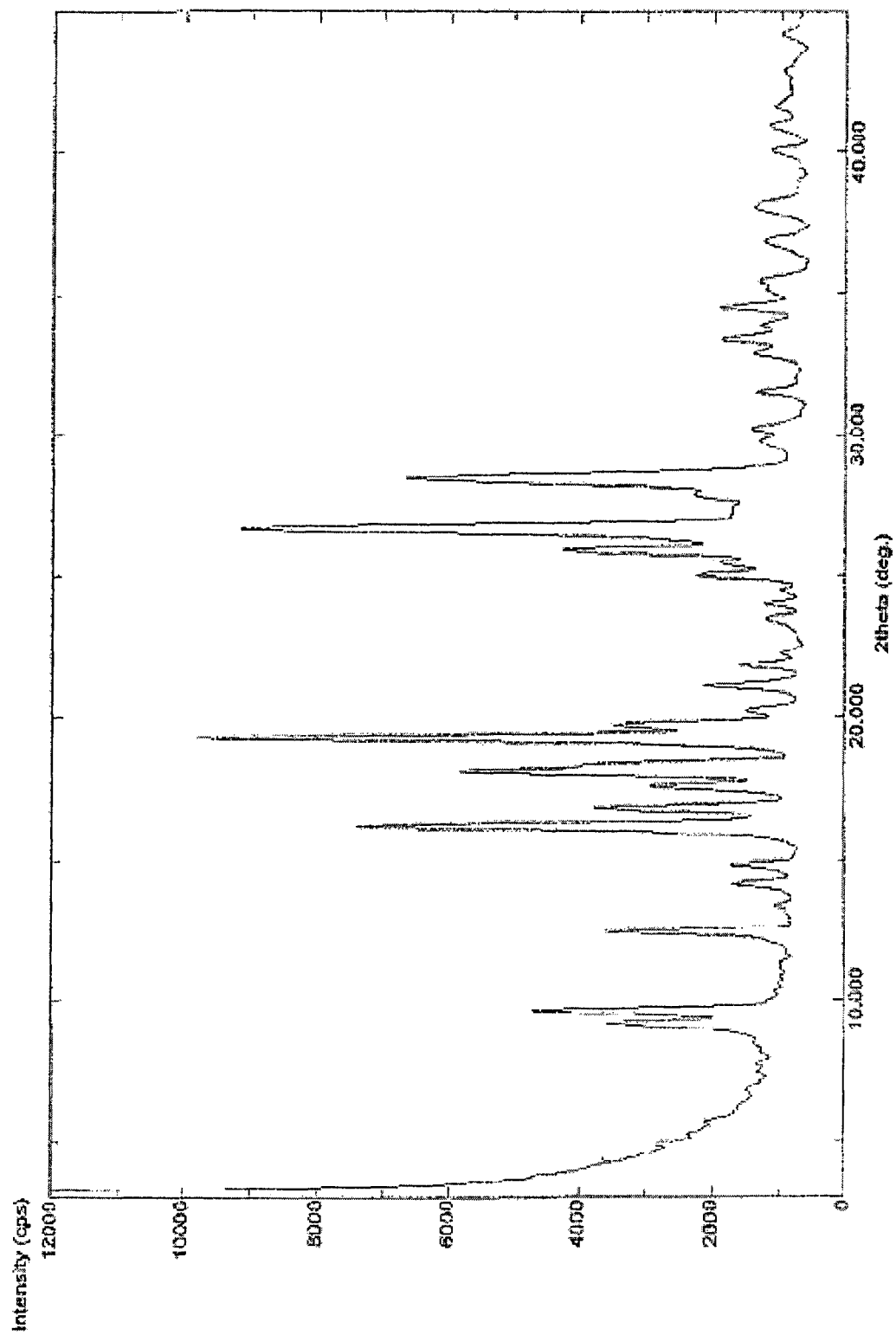
FIG. 10 is the characteristic powder. X-ray diffraction (XRD) pattern of Lamivudine caffeate Form I.

In another embodiment, the present invention further provides Lamivudine caffeate in crystalline Form I characterized by an X-Ray diffraction (XRD) pattern substantially in accordance with FIG. 10.

In another embodiment, the present invention provides Lamivudine p-coumarate (2:1).

In another embodiment, the present invention provides Lamivudine p-coumarate (2:1) in crystalline Form I.

Figure 11:
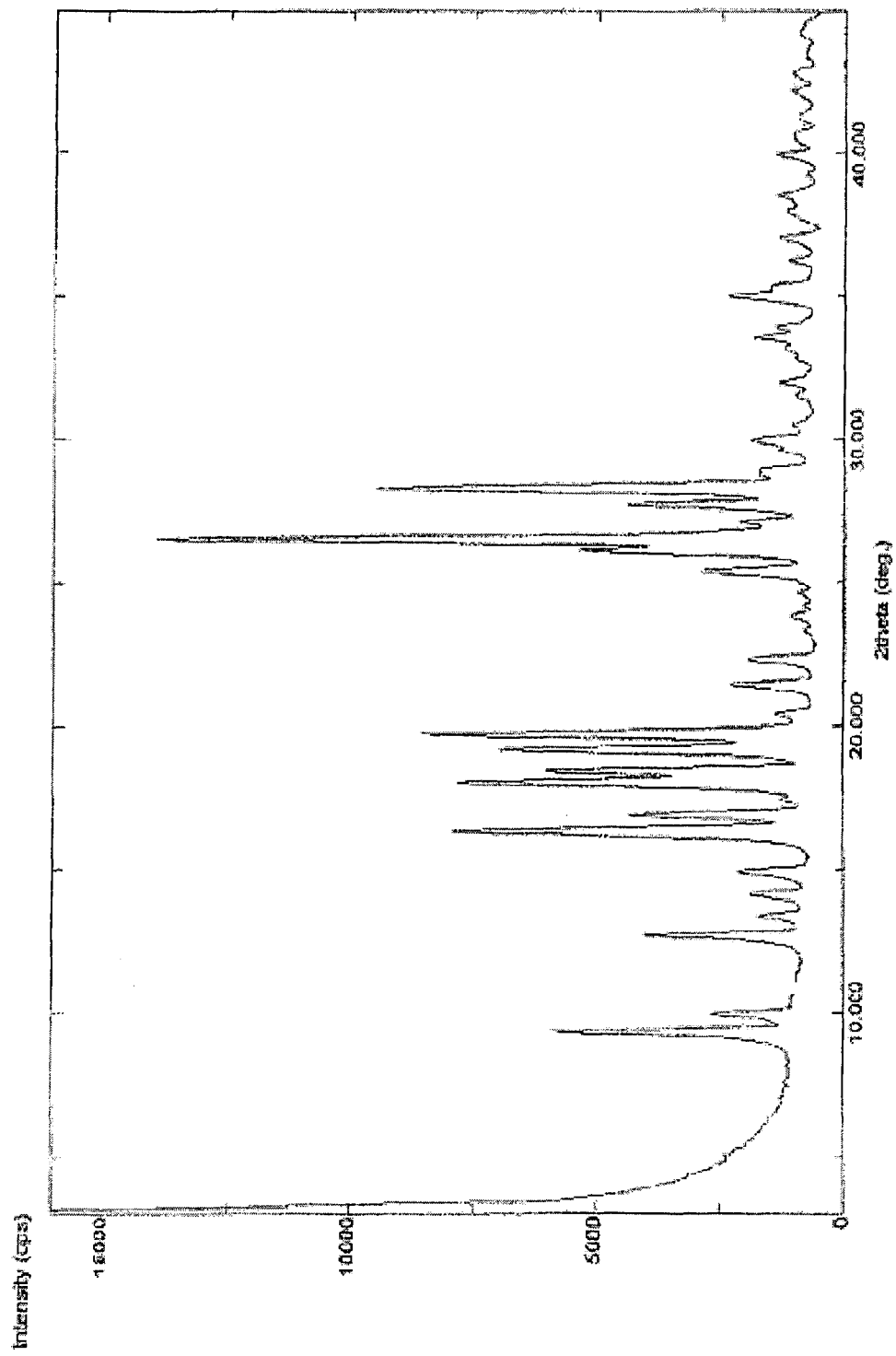
FIG. 11 is the characteristic powder X-ray diffraction (XRD) pattern of Lamivudine p-coumarate Form I.

In another embodiment, the present invention further provides Lamivudine p-coumarate (2:1) in crystalline Form I characterized by an X-Ray diffraction (XRD) pattern substantially in accordance with FIG. 11.

In another embodiment, the present invention provides Lamivudine p-coumarate (1:1).

In another embodiment, the present invention provides Lamivudine p-coumarate (1:1) in crystalline Form II.

Figure 12:
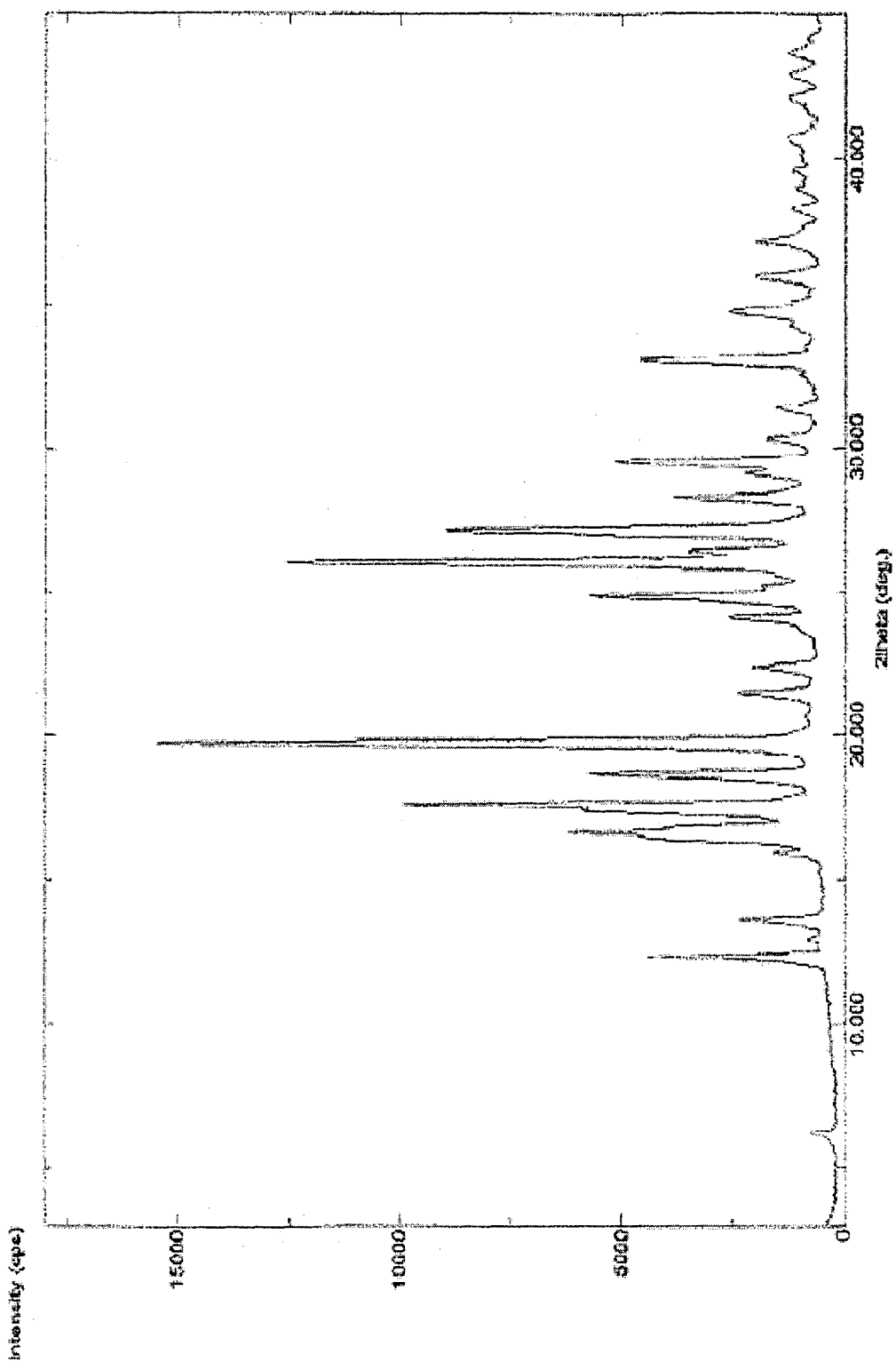
FIG. 12 is the characteristic powder X-ray diffraction (XRD) pattern of Lamivudine p-coumarate Form II.

In another embodiment, the present invention further provides Lamivudine p-coumarate (1:1) in crystalline Form II, characterized by an X-Ray diffraction (XRD) pattern substantially in accordance with FIG. 12.

In another embodiment, the present invention provides Emtricitabine ferulate.

In another embodiment, the present invention provides Emtricitabine ferulate in crystalline Form I.

Figure 13:
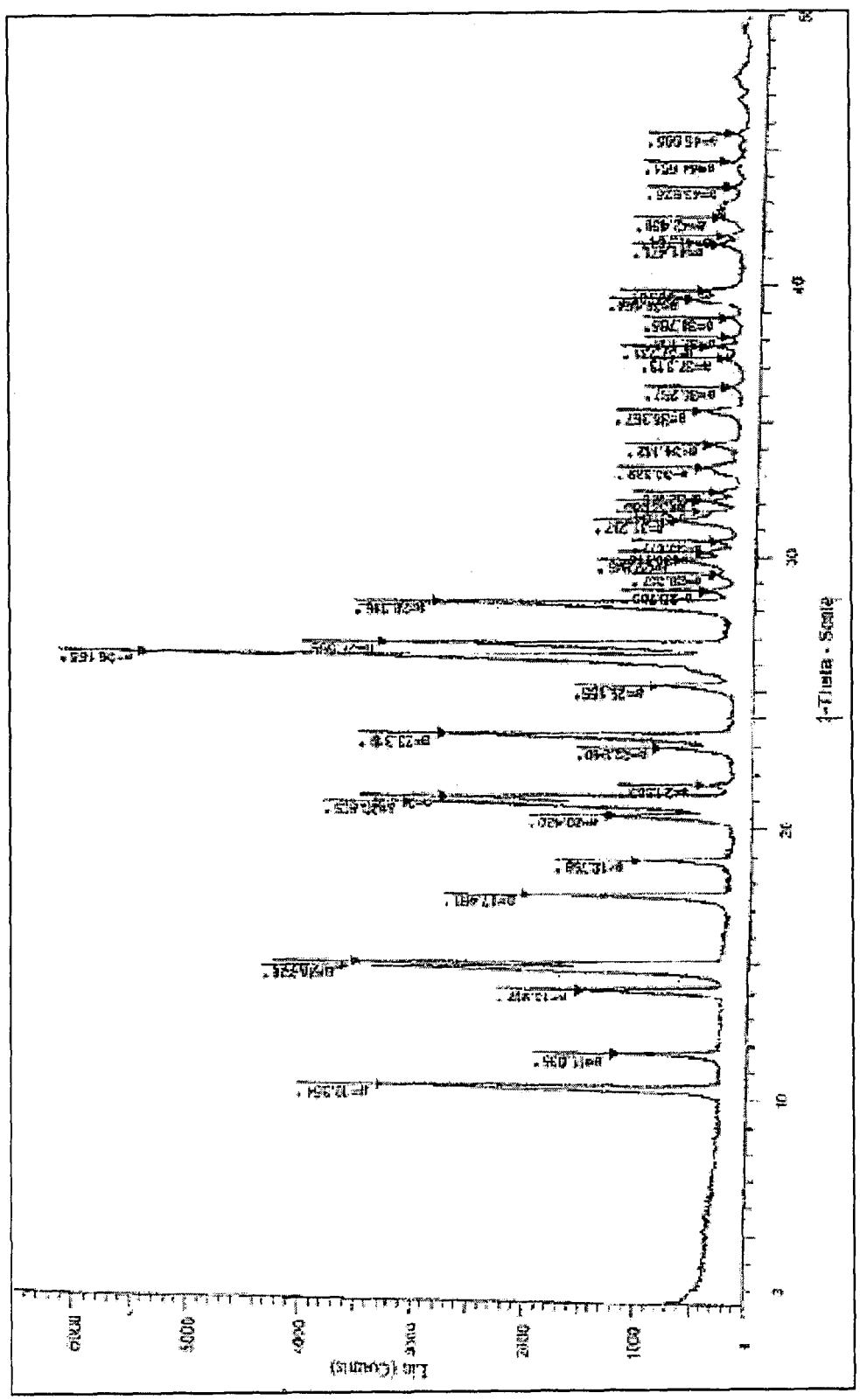
FIG. 13 is the characteristic powder X-ray diffraction (XRD) pattern of Emtricitabine ferulate Form I.

In another embodiment, the present invention further provides Emtricitabine ferulate in crystalline Form I, characterized by an X-Ray diffraction (XRD) pattern substantially in accordance with FIG. 13.

In another embodiment, the present invention provides Emtricitabine caffeate.

In another embodiment, the present invention provides Emtricitabine caffeate in crystalline Form I.

Figure 14:
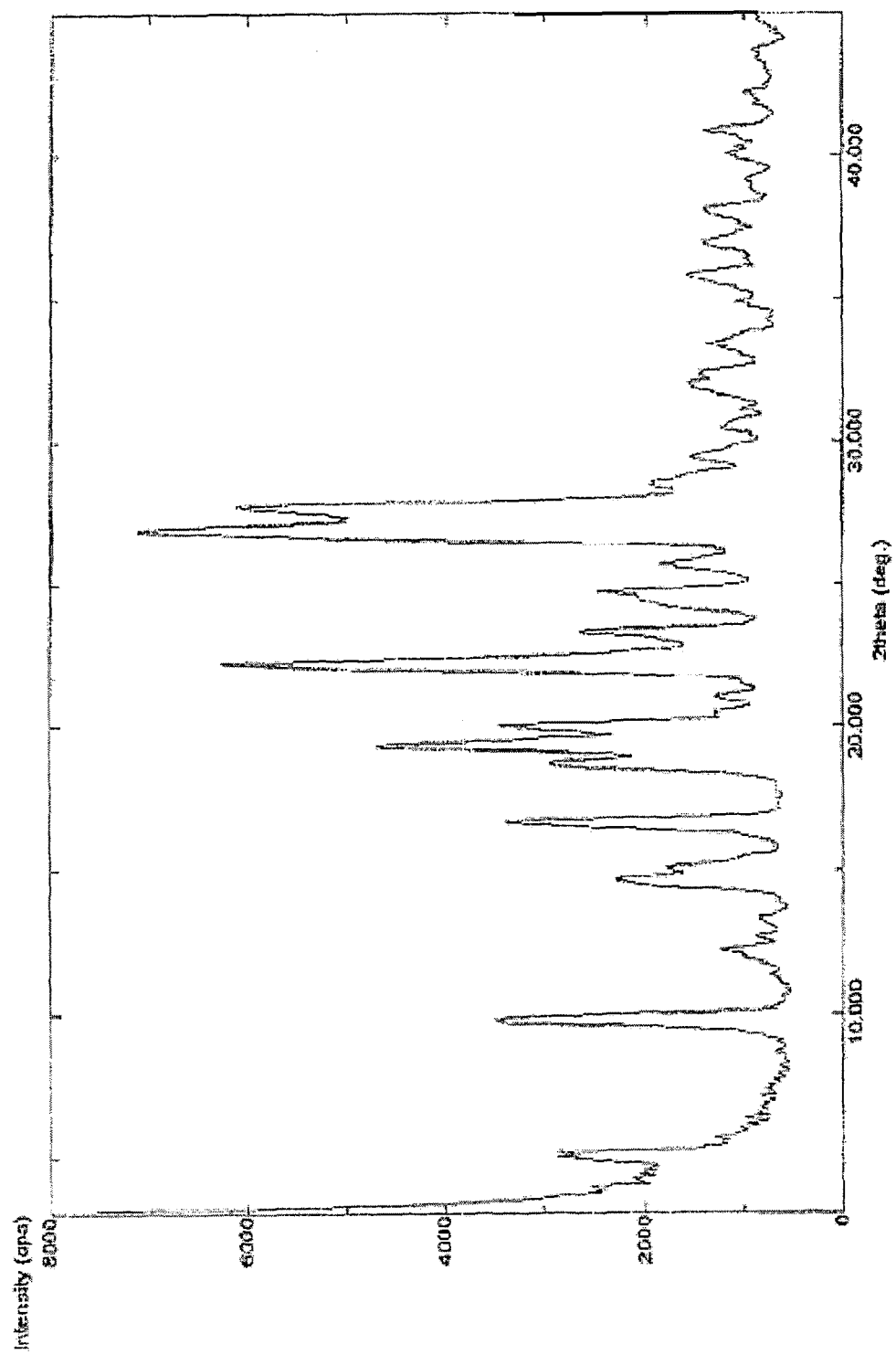
FIG. 14 is the characteristic powder X-ray diffraction (XRD) pattern of Emtricitabine caffeate Form I.

In another embodiment, the present invention further provides Emtricitabine caffeate in crystalline Form I characterized by an X-Ray diffraction (XRD) pattern substantially in accordance with FIG. 14.

In another embodiment, the present invention provides Emtricitabine caffeate in crystalline Form II.

Figure 15:
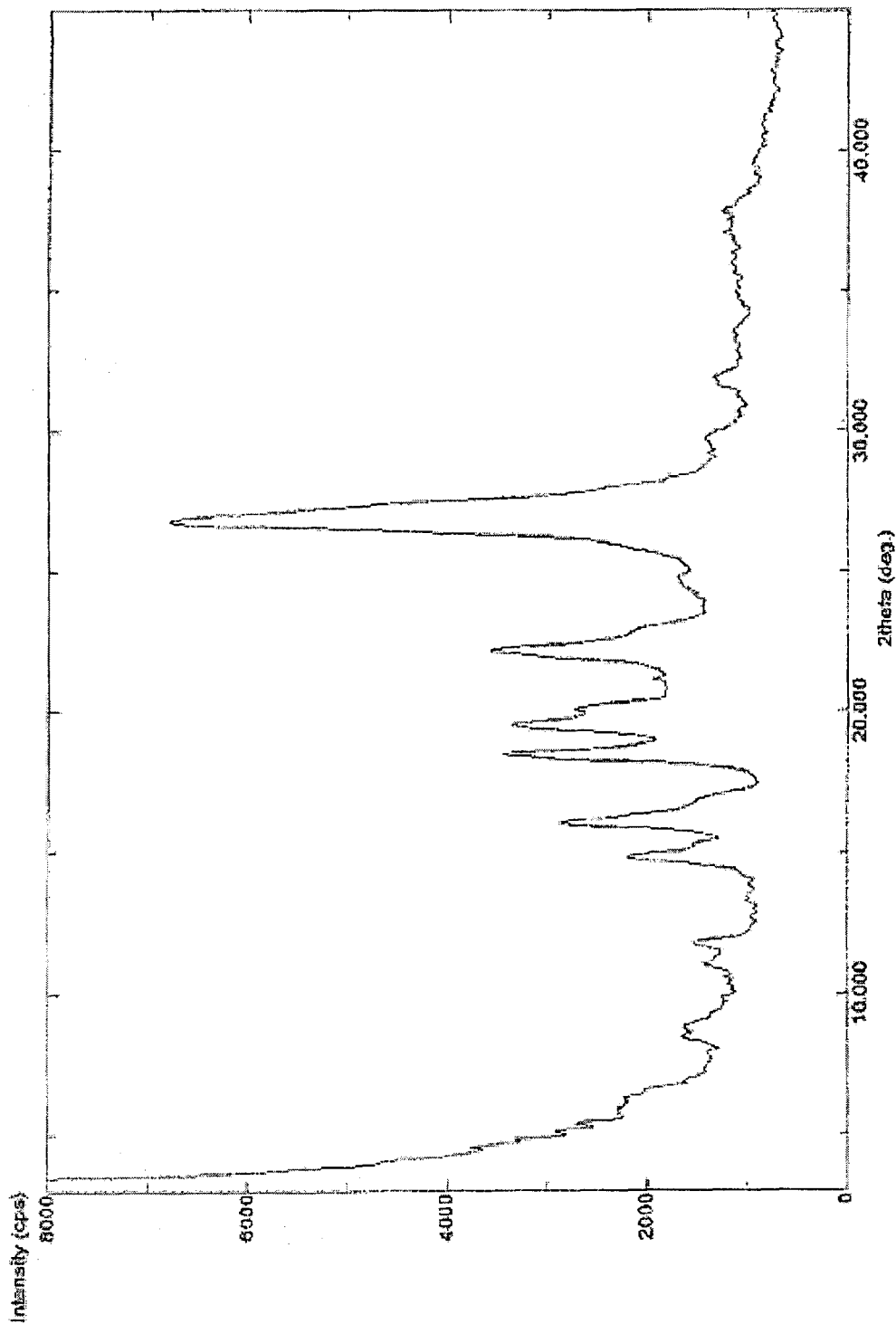
FIG. 15 is the characteristic powder X-ray diffraction (XRD) pattern of Emtricitabine caffeate Form II.

In another embodiment, the present invention further provides Emtricitabine caffeate in crystalline Form II, characterized by an X-Ray diffraction (XRD) pattern substantially in accordance with FIG. 15.

In another embodiment, the present invention provides Emtricitabine p-coumarate.

In another embodiment, the present invention provides Emtricitabine p-coumarate in crystalline Form I.

Figure 16:
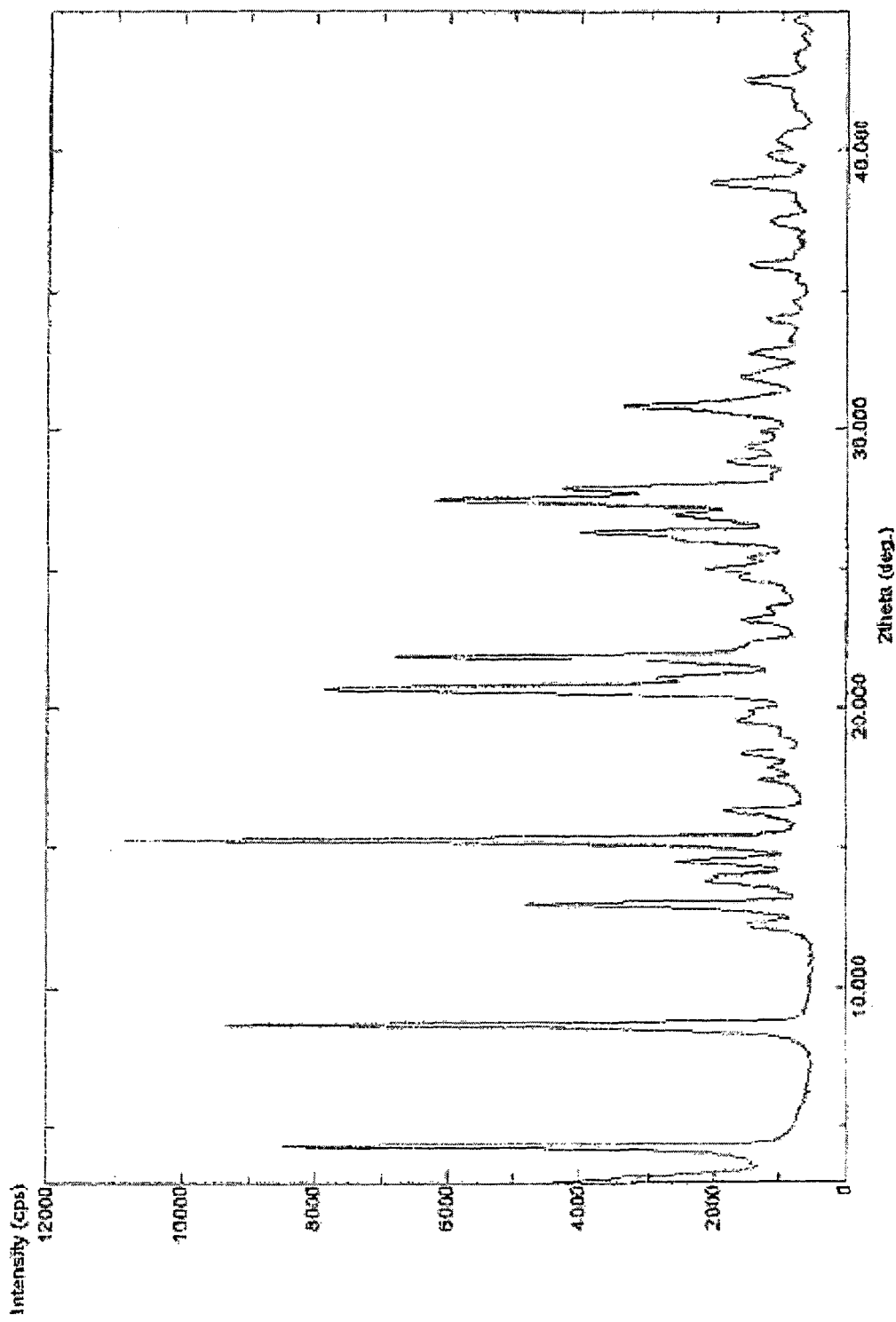
FIG. 16 is the characteristic powder X-ray diffraction (XRD) pattern of Emtricitabine p-coumarate Form I.

In another embodiment, the present invention further provides Emtricitabine p-coumarate in crystalline Form I, characterized by an X-Ray diffraction (XRD) pattern substantially in accordance with FIG. 16.

In another embodiment, the present invention provides Emtricitabine p-coumarate in crystalline Form II.

Figure 17:
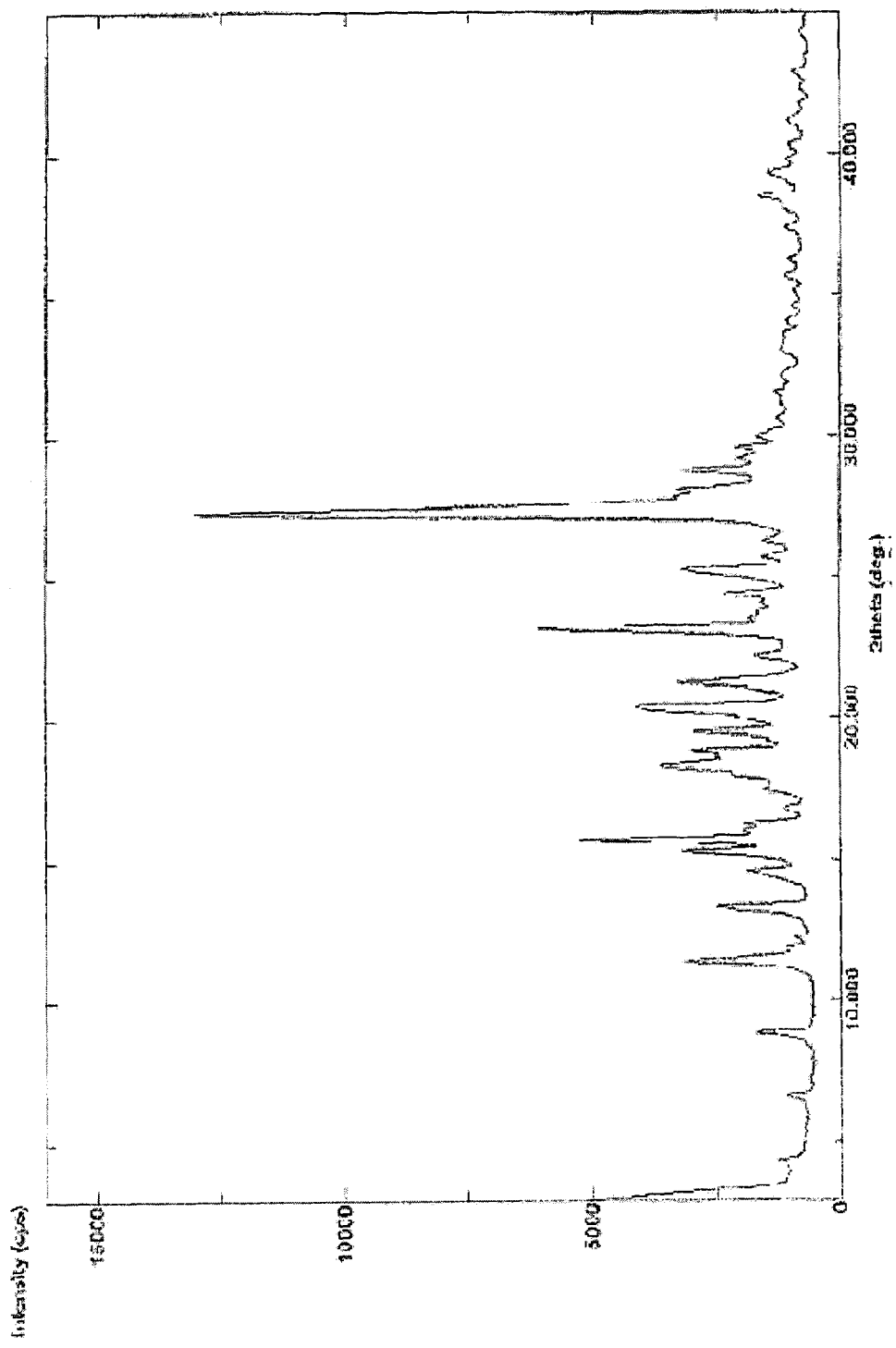
FIG. 17 is the characteristic powder X-ray diffraction (XRD) pattern of Emtricitabine p-coumarate Form II.

In another embodiment, the present invention further provides Emtricitabine p-coumarate in crystalline Form II, characterized by an X-Ray diffraction (XRD) pattern substantially in accordance with FIG. 17.

In another embodiment, the present invention provides Emtricitabine p-coumarate in crystalline Form III.

Figure 18:
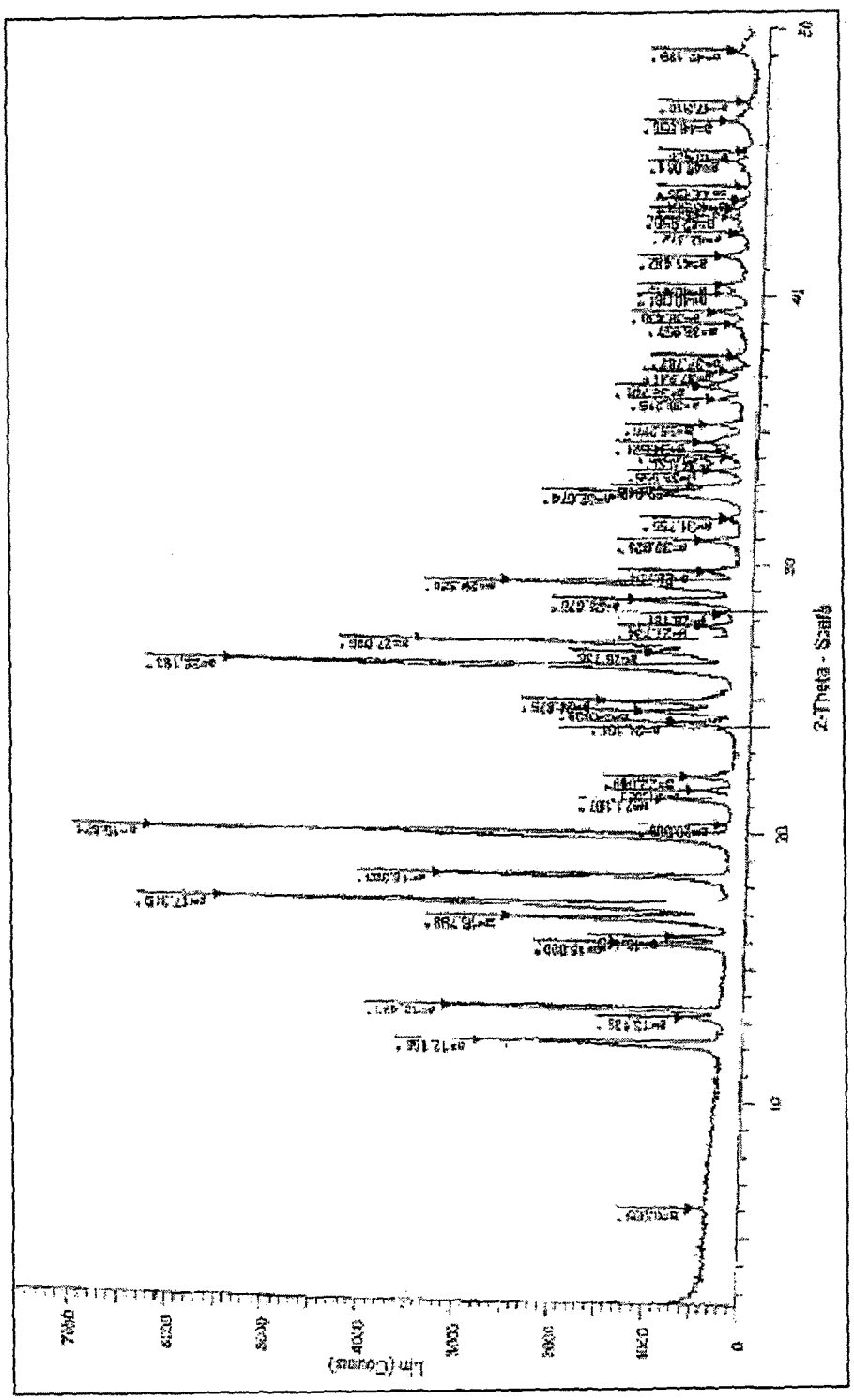
FIG. 18 is the characteristic powder X-ray diffraction (XRD) pattern of Emtricitabine p-coumarate Form III.

In another embodiment, the present invention further provides Emtricitabine p-coumarate in crystalline Form III, characterized by an X-Ray diffraction (XRD) pattern substantially in accordance with FIG. 18.

In another embodiment, the present invention provides Abacavir ferulate.

Figure 19:
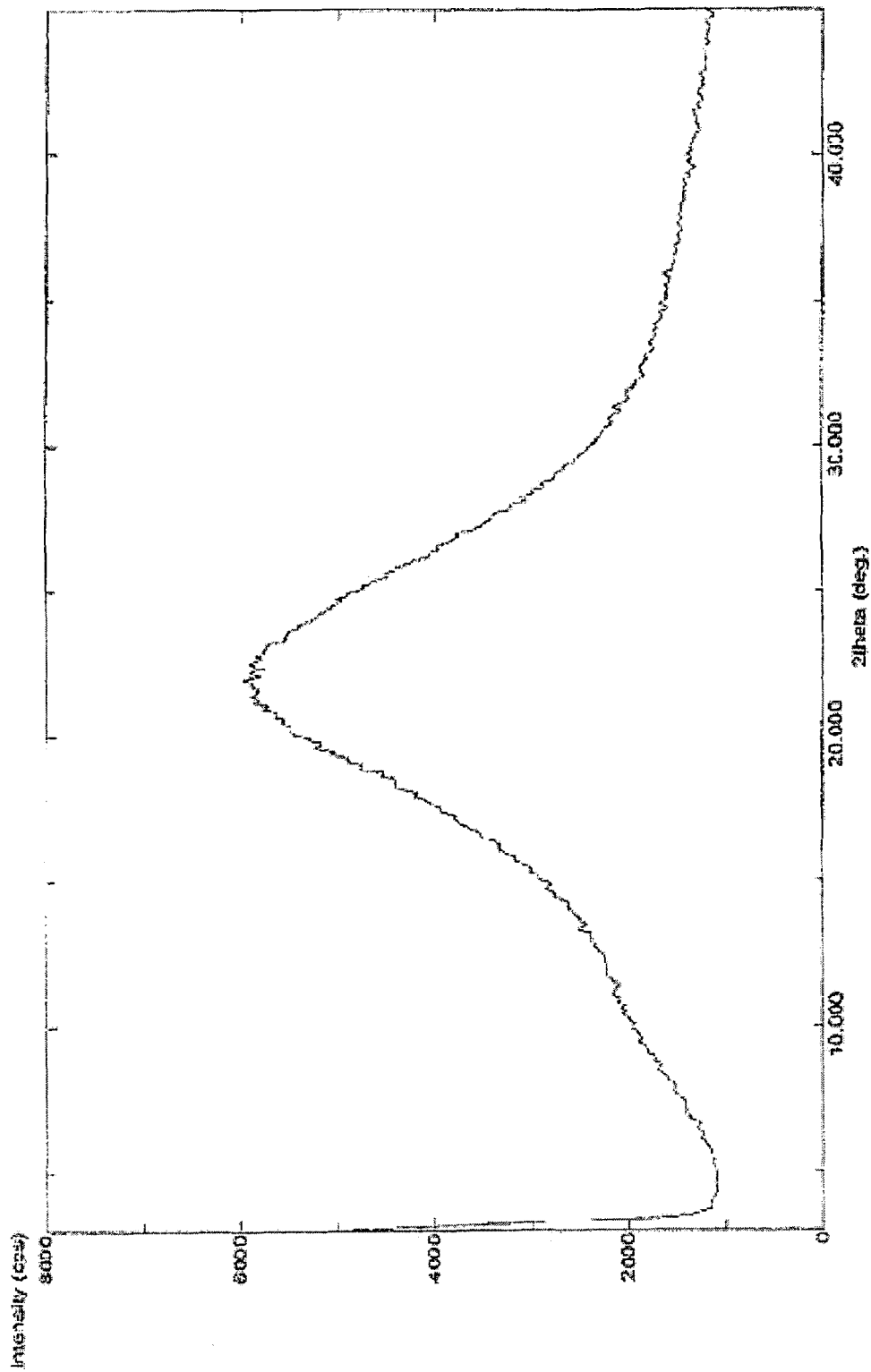
FIG. 19 is the characteristic powder X-ray diffraction (XRD) pattern of Abacavir ferulate.

In another embodiment, the present invention further provides Abacavir ferulate, characterized by an X-Ray diffraction (XRD) pattern substantially in accordance with FIG. 19.

In another embodiment, the present invention provides Abacavir caffeate.

Figure 20:
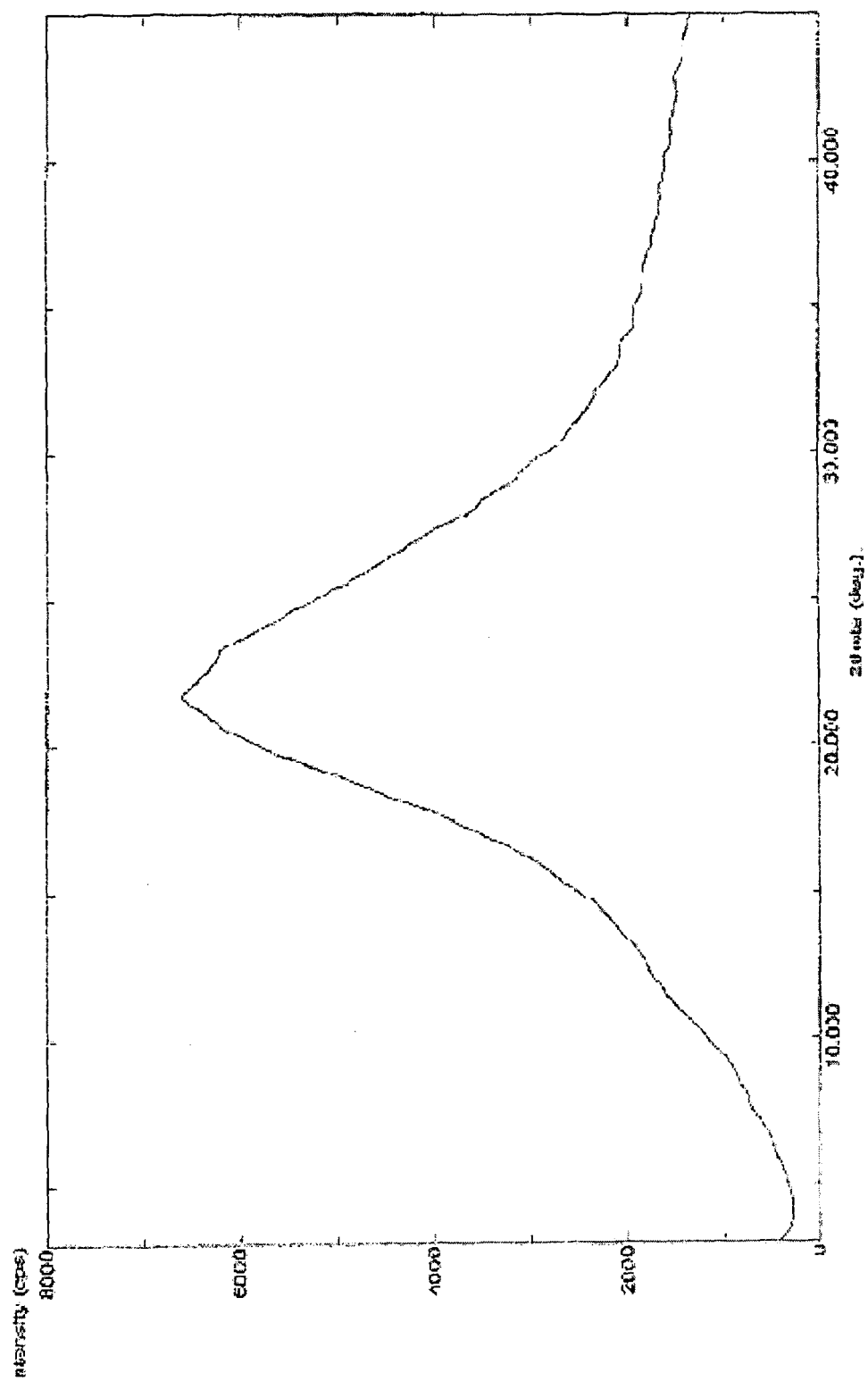
FIG. 20 is the characteristic powder X-ray diffraction (XRD) pattern of Abacavir caffeate.

In another embodiment, the present invention further provides Abacavir caffeate, characterized by an X-Ray diffraction (XRD) pattern substantially in accordance with FIG. 20.

In another embodiment, the present invention provides Abacavir p-coumarate.

Figure 21:
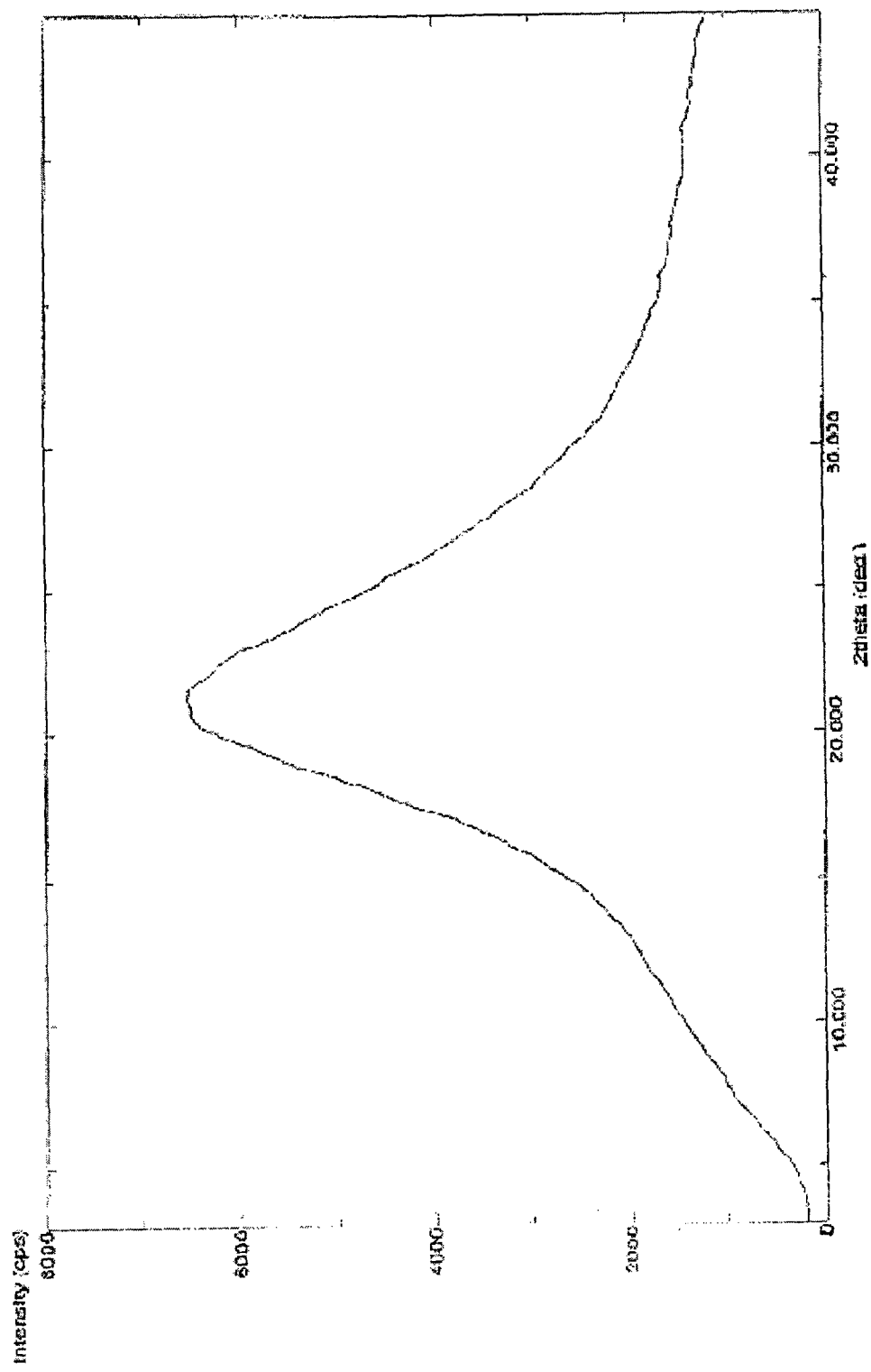
FIG. 21 is the characteristic powder X-ray diffraction (XRD) pattern of Abacavir p-coumarate.

In another embodiment, the present invention further provides Abacavir p-coumarate, characterized by an X-Ray diffraction (XRD) pattern substantially in accordance with FIG. 21.

The present invention provides characterization of solid forms of antiretroviral compounds of the present invention characterized by X-ray powder diffraction (XRD) pattern and/or melting point. The X-Ray powder diffraction can be measured by an X-ray powder Diffractometer equipped with a Cu-anode ($[\lambda]=1.54$ Angstrom), X-ray source operated at 40 kV, 30 mA and a Ni filter is used to strip K-beta radiation. Two-theta calibration is performed using an NIST SRM 640c Si standard. The sample was analyzed using the following instrument parameters: measuring range=2-50° 2θ; step width=0.032° and scan speed=3°/minute.

Alternatively, the X-Ray powder diffraction can be measured by an X-ray powder Diffractometer equipped with a Cu-anode ($[\lambda]=1.54$ Angstrom), X-ray source operated at 30 kV, 15 mA and a Ni filter is used to strip K-beta radiation.

Two-theta calibration is performed using an NIST SRM 640c Si standard. The sample was analyzed using the following instrument parameters: measuring range=3-45° 2θ; step width=0.020°; and scan speed=2°/minute.

In another embodiment, the present invention provides a pharmaceutical composition comprising a therapeutically effective amount of new solid forms of antiretroviral compounds; in particular combinations of antiretroviral compounds with anti-oxidative acids with at least one pharmaceutically acceptable carrier or other excipients.

The present invention further provides, when a pharmaceutical composition comprising solid forms of antiretroviral compounds prepared according to the present invention is formulated for oral administration or parenteral administration. Accordingly, D50 and D90 particle size of the unformulated solid forms of antiretroviral compounds of the present invention used as starting material in preparing a pharmaceutical composition generally is less than 400 microns preferably less than about 300 microns, more preferably less than 200 microns.

Any milling, grinding, micronizing or other particle size reduction method known in the art can be used to bring the solid forms of antiretroviral compounds of the present invention into any desired particle size range as set forth above.

Solid forms of antiretroviral compounds described in the present invention may be formulated into solid pharmaceutical products for oral administration in the form of capsules, tablets, pills, powders or granules. In these compositions, the active ingredient is combined with one or more pharmaceutically acceptable excipients. The drug substance also may be formulated into liquid compositions for oral administration including for example solutions, suspensions, syrups, elixirs and emulsions, containing solvents or vehicles such as water, sorbitol, glycerine, propylene glycol or liquid paraffins.

Compositions for parenteral administration may be suspensions, emulsions or aqueous or non-aqueous, sterile solutions. As a solvent or vehicle, propylene glycol, polyethylene glycol, vegetable oils, olive oil, and injectable organic esters, e.g. ethyl oleate, may be employed.

Suitable pharmaceutical compositions are solid dosage forms, such as tablets with immediate release or sustained release of the active principle, effervescent tablets or dispersion tablets and capsules.

Optionally, the pharmaceutical compositions of the invention may be combination products comprising one or more additional pharmaceutically active components in addition to solid forms of antiretroviral compounds of the present invention.

Pharmaceutically acceptable excipients include, but are not limited to, diluents such as starch, pregelatinized starch, lactose, powdered cellulose, microcrystalline cellulose, dicalcium phosphate, tricalcium phosphate, mannitol, sorbitol and sugar; binders such as acacia, guar gum, tragacanth, gelatin, polyvinylpyrrolidones, hydroxypropyl celluloses, hydroxypropylmethyl celluloses and pregelatinized starch; disintegrants such as starch, sodium starch glycolate, pregelatinized starch, crospovidones, croscarmellose sodium and colloidal silicon dioxide; lubricants such as stearic acid, talc, magnesium stearate and zinc stearate; glidants such as colloidal silicon dioxide; solubility or wetting enhancers such as anionic or cationic or neutral surfactants, complex forming agents such as various grades of cyclodextrins and resins; release rate controlling agents such as hydroxypropyl celluloses, hydroxymethyl celluloses, hydroxypropyl methylcelluloses, ethyl celluloses, methyl celluloses, various grades of methyl methacrylates, and waxes. Other pharmaceutically acceptable excipients that are of use include but are not limited to film formers, film coating agents, plasticizers, colorants, flavoring agents, sweeteners, viscosity enhancers, preservatives, and antioxidants.

Unless defined otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described.

Unless stated to the contrary, any use of the words such as "including," "containing," "comprising" and the like, means "including without limitation" and shall not be construed to limit any general statement that it follows to the specific or similar items or matters immediately following it. Embodiments of the invention are not mutually exclusive, but may be implemented in various combinations.

For purposes of the present invention, the following terms are defined below.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s), and pharmaceutically acceptable excipients.

The term "co-crystal" as used herein means a crystalline material comprised of two or more unique solids at room temperature, each containing distinctive physical characteristics, such as structure, melting point and heats of fusion.

The following non limiting examples illustrate specific embodiments of the present invention. They are not intended to be limiting the scope of the present invention in any way.

EXAMPLES

Example 1: Preparation of Tenofovir Disoproxil Ferulate Form AL1

Charged 10 gms of Tenofovir disoproxil, 3.74 gms of ferulic acid and 60 ml of isopropyl alcohol in a round bottom flask at temperature 25° C. to 35° C. Heated to 45° C. to 50° C. to form a clear solution and maintained for 15 minutes. The resultant solution was cooled to 25° C. to 30° C. and added 340 ml of Water for 30 minutes. The reaction mass was maintained for 2 hrs at same temperature and filtered the resultant product. The wet product was dried under vacuum at 40°-45° C. for 2 hrs to afford 8 gms of the title compound.
HPLC purity: 98.30%
The XRPD is set forth in FIG. 1.

Example 2: Preparation of Tenofovir Disoproxil Ferulate

Charged 10 gms of Tenofovir disoproxil, 3.74 gms of ferulic acid and 50 ml of Acetone at 25° to 30° C. and heated to 55° C.-60° C. to form a clear solution. The resultant solution was cooled to 25° C.-30° C. and added 250 ml of cyclohexane for 30 minutes. The reaction mass was kept at room temperature without stirring for 30 minutes. The precipitated solid was filtered and dried at 45°-50° C. for 2 hrs to afford 10 gms of crystalline solid.

Example 3: Preparation of Tenofovir Disoproxil Ferulate Form AL1

Slurried 1 gm of Tenofovir disoproxil ferulate (obtained from example-2) and 25 ml of DM water at 25° C.-35° C. for 10 hrs. The obtained solid was filtered and dried at 40° C.-45° C. for 1 hr to afford 0.4 gm of the title compound.
The XRPD is set forth in FIG. 1.

Example 4: Preparation of Tenofovir Disoproxil Ferulate Form AL2

Slurried 8 gms of Tenofovir disoproxil ferulic acid (obtained from example-2) and 40 ml of IPA at 25° C.-35° C. for 24 hrs. The obtained solid was filtered and dried at 45° C.-50° C. for 1 hr to afford 4 gms of the title compound.
The XRPD is set forth in FIG. 2.

Example 5: Preparation of Tenofovir Disoproxil Ferulate Form AL2

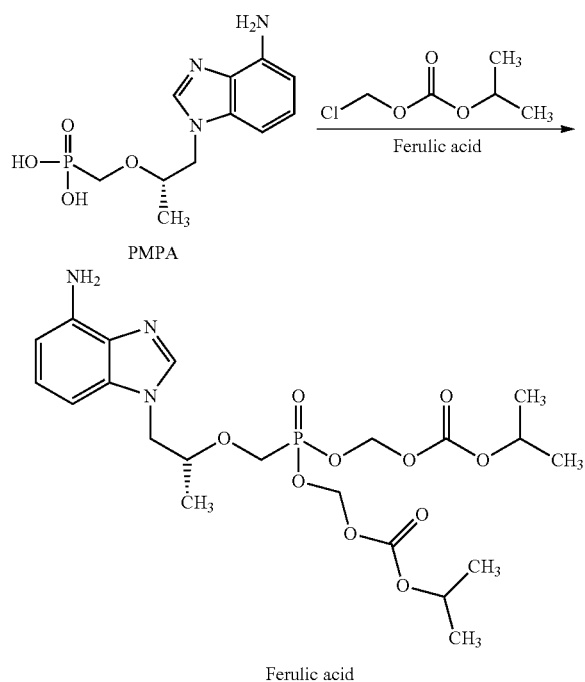

Into a 2 liter 4 necked round bottom flask fitted with a mechanical stirrer and a reflux condenser was charged 10 gms of PMPA, 80 ml of cyclohexane, 6.7 gms of triethylamine at temperature 25° C. to 30° C. Heated to 80° C. to 85° C. and maintained at same temperature to removed water azeotropically. Solvent was removed completely under vacuum at temperature below 85° C. To the resultant mass, charged 30 ml of N-Methyl pyrrolidinone, 6.7 gms of triethyl amine at 25° C. to 30° C. and stirred for 60 minutes at same temperature. Charged 5.3 gms of Tetrabutyl ammonium bromide (TBAB) and heated to 50° C. to 55° C. and added 20 gms of Chloro methyl isopropyl carbonate (CMIC) and stirred for 3 hours at same temperature and again added 5 gms of CMIC and stirred for further 30 minutes. After completion of the reaction by HPLC, cooled the reaction mass to 20° C. to 25° C. and washed with cyclohexane (2×40 ml). The reaction mixture was diluted with 100 ml of dichloromethane and stirred for 60 minutes at 10° C. to 15° C. Filtered the precipitate and washed filtrate with DM water (7×50 ml). Charged 100 ml of DM water to the organic layer and adjusted the pH to 6.5-7.5 with 10% ammonia solution at 10° C. to 15° C. Separated the organic layer and evaporated completely under vacuum at temperature below 35° C. The residue co evaporated with ethyl acetate (10 ml) and the semi solid obtained was dissolved in IPA (25 ml).

In another round bottom flask charged 6.4 gms of ferulic acid and 45 ml of IPA at temperature 25° C. to 30° C. Heated to 50° C. to 55° C. and added to the above solution of semisolid in IPA and stirred for 30 minutes at same temperature. Cooled the resultant solution to 35° C. to 40° C. and seeded with Tenofovir disoproxil ferulate (around 50 mg) followed by further cooling to 30° C. to 35° C. Further cooled the solution to 25° C. to 30° C. and stirred for 60 minutes and then cooled to 0° C. to 5° C. Stirred for 4 hours at 0° C. to 5° C. and filtered the precipitated solid and slurred with 10 ml of IPA. The wet product was dried at 35° C. to 40° C. under reduced pressure for 6 hours to provide the title compound as crude (yield: 12 gms)

Charged 12 gms of the resultant dry compound in 50 ml of isopropanol, 3 ml of ethyl acetate at temperature 10° C. to 15° C. Stirred for 60 minutes at same temperature and filtered the product and washed with 10 ml of isopropanol. The wet product was dried at 35° C. to 40° C. under reduced pressure for 6 hours to provide the title compound (yield: 9 gms).
HPLC purity: 99.1%
The XRPD is set forth in FIG. 2.

Example 6: Preparation of Tenofovir Disoproxil Ferulate Form AL2 from Tenofovir Disoproxil Fumarate Charged 25 gms of Tenofovir disoproxil fumarate, 125 ml of DM water, 125 ml of dichloromethane in to a 2 liter 4 necked round bottom flask fitted with a mechanical stirrer and a reflux condenser at temperature 25° C. to 30° C. Adjust the pH to 7.0 with 10% ammonia solution and separated aqueous and organic layers. To the aqueous layer charged 25 ml of dichloromethane and extracted the product. Combined the organic layers and evaporated completely under vacuum below 35° C. to obtain residue. To the residue added 75 ml of IPA to the Tenofovir disoproxil base solution. In another round bottom flask, charged 75 ml of IPA and 7.7 gms of ferulic acid and above obtained Tenofovir disoproxil base solution at temperature 50° C. to 55° C. and stirred for 60 minutes at same temperature. Cooled the resultant solution to 35° C. to 40° C. and seeded with Tenofovir disoproxil ferulate (around 25 mg) followed by further cooling to 30° C. to 35° C. Further cooled the solution to 25° C. to 30° C. and stirred for 60 minutes and then cooled to 0° C. to 5° C. Stirred for 4 hours at 0° C. to 5° C. and filtered the precipitated solid and slurred with 10 ml of IPA. The wet product was dried at 35° C. to 40° C. under reduced pressure for 6 hours to provide the title compound (yield: 20 gms)

The XRPD is set forth in FIG. 2.

Example 7: Preparation of Tenofovir Disoproxil Ferulate Form AL3

Tenofovir Disoproxil (5 gm) and Ferulic acid (2.05 gm) were added to IPA (25 ml) at 25° C. and then heated to 40-45° C. to form a clear solution. Maintained the reaction mass for about 1 hour and then cooled to 25-30° C. and stirred for ½ hour. The obtained solid was filtered and dried at 40° C. for 2 hours to get solid state form of Tenofovir disoproxil ferulate (0.50 gm).

The XRPD is set forth in FIG. 3

Example 8: Preparation of Tenofovir Disoproxil Ferulate Form AL4

Tenofovir Disoproxil (0.5 gm) and Ferulic acid (0.16 gm) were added to IPA (3 ml) at 25° C. and then heated to 45-50° C. to form a clear solution. The reaction mass was set aside for slow solvent evaporation. After one week solid form of Tenofovir disoproxil ferulate was obtained.

The XRPD is set forth in FIG. 4

Example 9: Preparation of Tenofovir Disoproxil Ferulate Form AL5

Tenofovir Disoproxil (HPLC purity: 84%) (6 gm) was dissolved in ethyl acetate (30 ml) at 25-30° C. and then Ferulic acid (2.24 gm) was added. Stirred the reaction mass for 10 min till dissolution and heated the temperature of the reaction mass to 55-50° C. and stirred for 1 hour. Cooled the reaction mass to 0-5° C. and Cyclohexane (3 ml) was added to reaction mass (1 ml) in a test tube and stirred for 5 min at 25° C. and decant the solution. Obtained solids were poured back to the reaction mass and stirred for 2 hours. Filtered the obtained solid and dried at 30° C. for 6 hours to obtain Tenofovir disoproxil ferulate (5.6 gm).

The XRPD is set forth in FIG. 5

Example 10: Preparation of Tenofovir Disoproxil Caffeate Form I

Charged 5 gms of Tenofovir disoproxil, 1.73 gms of Caffeic acid and 25 ml of IPA into a round bottom flask at 25° to 35° C. Heated the resultant reaction mass to 55° C. to 60° C. to form a clear solution and then cooled to 25° to 35° C. and added 200 ml of DM water for 40 minutes. The reaction mass was maintained for 2 hrs at 25° to 35° C. and the precipitated solid was filtered and dried at 40° C. to 45° C. for 3 hours to afford 4.78 gms of the title compound.

The XRPD is set forth in FIG. 6.

Example 11: Preparation of Tenofovir Disoproxil Caffeate Form I

Charged 1 gm of Tenofovir disoproxil, 0.347 gms of Caffeic acid and 5 ml of IPA into a round bottom flask at 25° to 35° C. Heated the resultant reaction mass to about 55° C. to 60° C. to form a clear solution and then cooled to −5° to −10° C. Added 30 ml of DM water for 5 minutes. The reaction mass was maintained for 2 hrs at −5° to −10° C. and raised temperature to 25° C. to 30° C. and maintained for 2 hours at same temperature. Added 10 ml of DM Water to the precipitated product and maintained for 15 minutes at same temperature. The precipitated solids were filtered and dried at 40° C. to 45° C. for 1 hour to afford 0.5 gms of the title compound.

HPLC Purity: 98.70%

The XRPD is set forth in FIG. 6.

Example 12: Preparation of Tenofovir Disoproxil Caffeate Form II

Tenofovir Disoproxil (3 gm) and Caffeic acid (1.1 gm) were added to IPA (15 ml) at 25° C. and then heated to 55-60° C. to form a clear solution. The reaction mass was maintained to 1 hour at 55-60° C. Then the solution was cooled to 0-5° C. and maintained for 2 hours. The reaction mass was completely distilled off and swapped with hexane (15 ml). The crude residue was dissolved in dichloromethane (12 ml) and added slowly to the hexane (30 ml) for 10 min. Material precipitation was observed after 1 hour and stirred for 15 hrs. Filtered the solid and dried at 40° C. for 2 hours to obtain Tenofovir disoproxil caffeate (1.5 gm).

The XRPD is set forth in FIG. 7.

Example 13: Preparation of Tenofovir Disoproxil p-Coumarate Form I

Charged 5 gms of Tenofovir disoproxil, 1.58 gms of p-coumaric acid and 25 ml of Tetrahydrofuran in a round bottom flask at temperature 25° C. to about 35° C. and heated to 60° C. to 65° C. to form a clear solution. The solution was cooled to 25° C. to 30° C. and added 100 ml of cyclohexane for 30 minutes. The reaction mass was maintained for 2 hr at 25° C. to 30° C. The precipitated solids were filtered and dried at 40° C. to 45° C. for 2 hrs to afford 6.25 gms of the title compound.

HPLC: 98.25%

The XRPD is set forth in FIG. 8.

Example 14: Preparation of Tenofovir Disoproxil p-Coumarate Form I

Charged 3 gms of Tenofovir disoproxil, 0.948 gms of p-coumaric acid and 15 ml of acetonitrile in a round bottom flask at temperature 25° C. to about 35° C. and heated to 60° C. to 65° C. to form a clear solution. The solution was cooled to −15° C. to −20° C. and stirred for 30 minutes. The precipitated solid was filtered and dried at 40° C. to 45° C. for 2 hrs to afford 2.6 gms of the title compound.

HPLC purity: 99.06%

The XRPD is set forth in FIG. 8.

Example 15: Preparation of Tenofovir Disoproxil Sinapate Form I

Charged 3 gms of Tenofovir disoproxil, 1.29 gms of sinapic acid and 15 ml of Tetrahydrofuran at 25° C. to 35° C. in to a round bottom flask and heated to 60° C. to 65° C. to form a clear solution. The resultant solution was cooled to 25° C. to 30° C. and added 75 ml of Isopropyl ether for 30 minutes. The reaction mass was maintained for 3 hrs at 25° C. to 30° C. and precipitated solid was filtered and dried at 40° C. to 45° C. for 1 hour to afford 3.9 gms of the title compound.

HPLC Purity: 98.57%.
The XRPD is set forth in FIG. 9.

Example 16: Preparation of Tenofovir Disoproxil Sinapate Form I

Charged 0.5 gms of Tenofovir disoproxil, 0.216 gms of sinapic acid and 2.5 ml of Tetrahydrofuran in to a round bottom flask at 25° C. to 35° C. Heated the reaction mixture to 60° C. to 65° C. to form a clear solution and then the solution was cooled to 25° C. to 30° C. Added 12.5 ml of hexane for 10 minutes and maintained for 1 hr at 25° C. to 30° C. The precipitated solid was filtered and dried for 10 minutes to afford 0.57 gms of the title compound.
HPLC Purity: 98.51%.
The XRPD is set forth in FIG. 9.

Example 17: Preparation of Lamivudine Caffeate Form I

Charged 3 gms of Lamivudine, 2.35 gms of caffeic acid and 24 ml of methanol in to a round bottom flask at 25° C. to 35° C. and heated to 60° C. to 65° C. to form a clear solution. The reaction mass was kept for 18 hours without stirring and obtained solid was filtered to afford 3.5 gms of the title compound.
HPLC purity: 99.82%
The XRPD is set forth in FIG. 10.

Example 18: Preparation of Lamivudine p-Coumarate (2:1) Form I 0.5 gms of Lamivudine and 0.358 gms of p-coumaric acid were dissolved in 3 ml of methanol at 60° C. to 65° C. Cooled the resultant solution to 25° C. to 35° C. and kept for 2 hours at same temperature without stirring. The obtained solid was filtered and dried at 40° C. to 45° C. for 2 hours to afford 0.58 gms of the title compound.
HPLC purity: 99.83%
The XRPD is set forth in FIG. 11.

Example 19: Preparation of Lamivudine p-Coumarate (1:1) Form II 2 gms of Lamivudine and 1.43 gms of p-coumaric acid were taken in a mortar and pestle and the mixture was vigorously grounded for 2 hrs followed by addition of few drops of methanol in regular intervals. The product obtained was dried at 45° C. for 1 hour to afford 2.5 gms of the title compound.
The XRPD is set forth in FIG. 12.

Example 20: Preparation of Emtricitabine Ferulate Form I

Charged 10 gms of Emtricitabine 7.85 gms of ferulic acid and 100 ml of methanol in to a round bottom flask at 25° C. to 35° C. Heated to 64° C. to 70° C. to form a clear solution and maintained for 10 minutes at the same temperature. Cooled the resultant solution to 0° C.-5° C. and stirred for 5 minutes at same temperature. Filtered the precipitated solid and dried at 60° C. to 65° C. for 2 hours to afford 13.02 gms of the title compound.
HPLC Purity: 99.85%
The XRPD is set forth in FIG. 13.

Example 21: Preparation of Emtricitabine Caffeate Form I

Charged 5 gms of Emtricitabine, 3.64 gms of caffeic acid and 45 ml of methanol in to a round bottom flask at 25° C. to 35° C. and heated to 60° C. to 65° C. to form a clear solution. Then the solution cooled to 0°-5° C. and stirred for 30 minutes followed by raised temperature to 25° C. to 30° C. and stirred for 24 hours. The obtained solids were filtered and dried at 60° C. to 65° C. for 3 hours to afford 4 gms of the title compound.
The XRPD is set forth in FIG. 14.

Example 22: Preparation of Emtricitabine Caffeate Form II

Charged 1 gm of Emtricitabine, 0.728 gms of caffeic acid and 17 ml of ethanol at 25° C. to 35° C. and heated to 70° C. to 75° C. to form a clear solution. The reaction solution was partly distilled off by applying vacuum till the solids precipitated and filtered off the solids followed by drying at 60° C. to 65° C. for 3 hours to afford 0.86 gms of the title compound.
The XRPD is set forth in FIG. 15.

Example 23: Preparation of Emtricitabine Coumarate Form I

Dissolved 0.3 gms of Emtricitabine, 0.199 gms of p-coumaric acid in 4.5 ml of methanol at 60° C. to 65° C. and the reaction mass was kept at 25° C. to 35° C. for 69 hours. Then the resultant solids scratched to afford 0.5 gms of the title compound.
HPLC Purity: 99.17%
The XRPD is set forth in FIG. 16.

Example 24: Preparation of Emtricitabine Coumarate Form II 0.3 gms of Emtricitabine and 0.199 gms of p-coumaric acid were dissolved in 5 ml of ethanol at 60° C. to 65° C. and the reaction mass was kept at 25° C. to 35° C. for 70 hours. Then resultant solid material was filtered and suck dried for 20 minutes to afford 0.5 gms of the title compound.
HPLC Purity: 99.30%
The XRPD is set forth in FIG. 17.

Example 25: Preparation of Emtricitabine Coumarate Form III 2 gms of Emtricitabine and 1.328 gms of p-coumaric acid were added to 16 ml of Methanol at 25° C. to 35° C. and hated to 65° C. to 70° C. to form a clear solution. Then the reaction mass was cooled to 5° C.-10° C. and filtered the precipitated solid material and dried at 60° C. to 65° C. for 1 hour 30 minutes to afford 2.62 gms of the title compound.
The XRPD is set forth in FIG. 18

Example 26: Preparation of Abacavir Ferulate Amorphous Form 1 gm of Abacavir and 0.678 gms of ferulic acid were dissolved in 5 ml of methanol at 60° C. to 65° C. The resultant clear solution was evaporated completely under vacuum at 50° C. to 55° C. and obtained solids were collected to afford 1.2 gms of the title compound.

The XRPD is set forth in FIG. 19.

Example 27: Preparation of Abacavir Caffeate Amorphous Form 2.5 gm of Abacavir and 1.57 gms of caffeic acid were dissolved in 10 ml of methanol at 60° C. to 65° C. Then the resultant clear solution was evaporated completely under vacuum at 50° C. to 55° C. and obtained solids were collected to afford 2.65 gms of the title compound.

The XRPD is set forth in FIG. 20.

Example 28: Preparation of Abacavir p-Coumarate Amorphous Form 3 gms of Abacavir and 1.72 gms of p-coumaric acid were dissolved in 7 ml of methanol at 60° C. to 65° C. The resultant clear solution was evaporated completely under vacuum at 50° C. to 55° C. and obtained solids were collected to afford 3.15 gms of the title compound.

The XRPD is set forth in FIG. 21.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A composition comprising tenofovir disoproxil caffeate or tenofovir disoproxil p-coumarate wherein the tenofovir disoproxil caffeate is characterized by a 1:1 ratio of tenofovir and caffeic acid, and by an X-Ray diffraction pattern in accordance with FIG. 6 or FIG. 7, and wherein the tenofovir disoproxil p-coumarate is characterized by X-Ray diffraction pattern in accordance with FIG. 8.

2. A process for preparing a solid composition containing tenofovir disoproxil caffeate or tenofovir disoproxil p-coumarate, wherein the tenofovir disoproxil caffeate is characterized by a 1:1 ratio of tenofovir and caffeic acid and by an X-Ray diffraction pattern in accordance with FIG. 6 or FIG. 7, and wherein the tenofovir disoproxil p-coumarate is characterized by an X-Ray diffraction pattern in accordance with FIG. 8, comprising: mixing, in solution, the tenofovir disoproxil with either caffeic acid or p-coumaric acid under crystallization conditions sufficient to produce the solid composition.

3. The process according to claim 2, wherein the mixing step further comprises:
    a) dissolving the tenofovir disoproxil in a solvent at a temperature to produce a solution;
    b) adding either caffeic acid or p-coumaric acid to the solution; and
    c) isolating the solid composition from the solution.

4. The process according to claim 3, wherein the solvent is selected from the group consisting of water, lower alcohols, ketones, esters, ethers, $C_{5-7}$ linear, branched or cyclic, saturated or unsaturated hydrocarbons, nitriles, halogenated hydrocarbons, and mixtures thereof.

5. The process according to claim 3, wherein the solvent is selected from the group consisting of methanol, ethanol, isopropanol, acetone, tetrahydrofuran, isopropyl ether, acetonitrile, hexane, cyclohexane, ethyl acetate, water, and mixtures thereof.

6. The process according to claim 3, further comprising: adding a second solvent and cooling the solution to precipitation or concentrating the solution prior to step c).

7. The process according to claim 6, wherein the second solvent is selected from the group consisting of water, ethers, cyclic hydrocarbons, and mixtures thereof.

8. The process according to claim 3, wherein the temperature is about 30° C. to about reflux.

9. The process according to claim 3, wherein the isolating step c) uses filtration.

* * * * *